(12) United States Patent
Shou et al.

(10) Patent No.: US 11,947,794 B2
(45) Date of Patent: Apr. 2, 2024

(54) DATA MANAGEMENT SYSTEM

(71) Applicant: KABUSHIKI KAISHA SHOFU, Kyoto (JP)

(72) Inventors: Kouji Shou, Kyoto (JP); Ryohei Kondo, Kyoto (JP); Taro Tsuboi, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 38 days.

(21) Appl. No.: 17/752,234

(22) Filed: May 24, 2022

(65) Prior Publication Data

US 2023/0013749 A1    Jan. 19, 2023

(30) Foreign Application Priority Data

May 27, 2021   (JP) .................. 2021-089362

(51) Int. Cl.
*G06F 3/06*   (2006.01)
(52) U.S. Cl.
CPC .......... *G06F 3/0604* (2013.01); *G06F 3/0637* (2013.01); *G06F 3/067* (2013.01)

(58) Field of Classification Search
CPC ....... G06F 3/0604; G06F 3/0637; G06F 3/067
See application file for complete search history.

(56) References Cited

FOREIGN PATENT DOCUMENTS

| JP | 6441419 | 12/2018 |
|---|---|---|
| JP | 6697200 | 5/2020 |
| JP | 6732354 | 7/2020 |

*Primary Examiner* — Yong J Choe
(74) *Attorney, Agent, or Firm* — Wenderoth, Lind & Ponack, L.L.P.

(57) ABSTRACT

A data management system comprises: an outsourcer terminal outsourcing a fabrication by an instruction document; an outsourcee terminal receiving outsourcing and/or sub-outsourcing; and a server device. The server device comprises: a data management unit managing a proprietary authority of data stored in a data storage unit; an order container storage unit storing an order container with which data stored in the data storage unit is correlated, for each order created in an order creation unit of the outsourcer terminal and/or the outsourcee terminal; and an order container management unit managing sharing of the order container, based on an instruction from an order container sharing authority management unit of the outsourcer terminal and/or the outsourcee terminal. The server device, for each order, correlates any format of data element stored with the order container, for management.

24 Claims, 16 Drawing Sheets

| | | | |
|---|---|---|---|
| XX CLINIC | | | IIN TARO |

NAME OF PATIENT

PATIENT ID

DATE OF ISSUE: June 12, 2020

OUTSOURCER CLINIC: XX CLINIC

OUTSOURCER DOCTOR: IIN TARO

RELATED CASE

CHOOSE OUTSOURCER

OUTSOURCER
OUTSOURCER ADDR.
DESIGN
FABRICATION METHOD
MATERIALS

SELECTABLE TECHNICAL MENUS
ACCORDING TO SKILL LEVELS

ORDER

DATA MANAGEMENT SYSTEM

CROSS-REFERENCE TO RELATED APPLICATION

The present application claims the priority of Japanese Patent Application No. 2021-089362 entitled "Data Management System", filed on May 27, 2021, of which contents are incorporated herein by reference in its entirety.

BACKGROUND

1. Technical Field

The present disclosure relates to a data management system managing instruction documents or other information at dental clinics or dental laboratories.

2. Related Art

It is commonly performed in dental treatment to request a dental laboratory to make dental technical products. Although an outsourcing contract is concluded between a dental clinic and a dental laboratory, a written or/and verbal contracts have hitherto been concluded. The outsourcing contract states reward amount, reward payment time, technical fee at the time of refabrication, termination clauses, etc. Each dental clinic and/or each dental laboratory has discussed with a plurality of facilities to conclude outsourcing contracts with respective contract contents. It is often necessary to refer to the outsourcing contract in the scene where a request for refabrication occurs, such as when the technical product is damaged. In the case of managing with paper media, there is a need to look for and refer to them. In the case of verbal contract, the dental clinic and the dental laboratory need to confirm both perceptions and, as necessary, discuss with each other to solve the problem with mutual agreements. In this manner, complicated management and/or discussion has conventionally been required.

In the case that a dental clinic requests for fabricating dental technical products, the dental clinic or/and the dental laboratory need to create and manage the instruction documents. These documents have traditionally been managed on paper, taking time to create, store, and manage large numbers of paper instruction documents and work records.

Since dental technical products need to be made while adjusting to suit each patient, checks and modifications are often repeated between a dental clinic and a dental laboratory. Although up until now telephones, e-mails, SMS, facsimiles, etc. have been used for communications between the dental clinic and the dental laboratory, due to no correspondence with instruction documents, the dental clinic and the dental laboratory have experienced troublesomeness of searching for and referring to the corresponding instruction documents each time. Since in this manner checks and modifications have been performed through telephones, e-mails, SMS, facsimiles, etc. between the dental clinic and the dental laboratory when fabricating dental technical products, complicated management has been required in order to correlate inquiries, revisions, etc. with the instruction documents.

Although orders for dental technical products are issued from a dental clinic to a dental laboratory, a technical product impossible to make may be requested depending on the equipment of the dental laboratory receiving the order. The dental clinic or the dental laboratory needs to find another dental laboratory or processing center capable of processing, to outsource part or all of the order to a secondary outsourcee, based on dentist's instruction documents. Request to the secondary contractor has hitherto needed a cumbersome procedure, such as asking the dental clinic to reissue another instruction document by telephone, e-mail, SMS, or facsimile, to revise the instruction document.

Although up till now prostheses or dentures have been made based on a plaster model that is created by taking an impression of the patient's oral cavity, the recent business form of the dental laboratory is changing with advanced digitization, such as acquiring 3D shape data with a 3D scanner, designing with CAD, and processing with CAD/CAM equipment. However, advancement of digitization leads to increase in type and amount of data handled than before, rendering correlation of outsourced order with data complicated.

In a dental laboratory, there is a case where a plurality of dental technicians divide labor when fabricating a single technical product. For example, this is the case when the roles are divided in the same dental laboratory by the plurality of dental technicians, such as one who designs a dental technical product, one who processes the designed dental technical product, and one who finishes the processed dental technical product. In such a case, it takes time and effort for data management when taking over the data and the status of progress output in each process regarding a plurality of dental technical products.

To address such a problem, Japanese Patent No. 6441419 specification describes a system capable of electronically issuing orders for dental technical products from a dental clinic or a dental laboratory to a processing center. The system described in Japanese Patent No. 6441419 specification, however, is a one-way ordering system from the user terminal to the processing center, with no consideration on communications between the dental clinic and the dental laboratory.

Japanese Patent No. 6732354 specification and Japanese Patent No. 6697200 specification describe a system electronically managing dental technical instruction sheets to allow checks and modifications on the dental technical instruction sheets. The system described in Japanese Patent No. 6732354 specification and Japanese Patent No. 6697200 specification is intended to facilitate the management of the dental technical instruction sheets, with no consideration on data or documents other than the dental technical instruction sheets, data that cannot be correlated with the dental technical instruction sheets, and data not to be shared with the counterpart facility.

Since dental technical products need to be made while adjusting to suit each patient, there occurs interchange of various data between a dental clinic and a dental laboratory. With recent advanced digitization in dental care fields, the amount of the data is increasing even at the start of outsourcing or even during the technical work, inducing complicated management.

SUMMARY OF INVENTION

In view of the above problems, the present invention provides a novel system capable of simplifying data sharing between a dental laboratory and a dental laboratory, as well as of reducing the time and effort required for data management.

The system of the present invention is a data management system which follows, including an outsourcer terminal, an outsourcee terminal, and a server device, in order to solve the above problems. The present invention is as follows.

Item 1

A data management system comprising: an outsourcer terminal outsourcing a fabrication by an instruction document; an outsourcee terminal receiving outsourcing and/or sub-outsourcing; and a server device, the outsourcer terminal, the outsourcee terminal, and the server device being connected via a network and sharing data with one another, the outsourcer terminal comprising:
a transmission unit transmitting data in the outsourcer terminal to the server device to store the data into a data storage unit of the server device;
an order creation unit creating an order container in an order container storage unit of the server device for each order, the data stored in the data storage unit being correlated with the order container;
an order management unit correlating the data stored in the data storage unit with the order container;
an order container sharing authority management unit sharing the order container with the outsourcee; and
a display unit displaying information saved in the server device,
the server device comprising:
the data storage unit storing data;
a data management unit managing a proprietary authority of data stored in the data storage unit;
the order container storage unit storing an order container with which the data stored in the data storage unit is correlated, for each order created in the order creation unit of the outsourcer terminal and/or an order creation unit of the outsourcee terminal;
an order container management unit managing sharing of the order container, based on an instruction from the order container sharing authority management unit of the outsourcer terminal and/or an order container sharing authority management unit of the outsourcee terminal; and
a notification unit, when modification and/or data addition is applied to the order container shared by the order container sharing authority management unit, issuing a notification to the outsourcer and/or the outsourcee,
the outsourcee terminal comprising:
a transmission unit transmitting data in the outsourcee terminal to the server device to store the data into the data storage unit of the server device;
the order creation unit creating an order container in the order container storage unit of the server device for each order, the data stored in the data storage unit being correlated with the order container;
an order management unit correlating the data stored in the data storage unit with the order container;
the order container sharing authority management unit sharing the order container with the outsourcer; and
a display unit displaying information saved in the server device,
for each order, any format of data element stored in the server device being correlated with the order container, for management.

Item 2

The data management system of item 1, wherein the outsourcer terminal and/or the outsourcee terminal comprises:
an outsourcing start application unit for starting outsourcing with the outsourcer terminal and/or the outsourcee terminal; and
an outsourcing start approval unit approving an application filed from the outsourcing start application unit, wherein
the server device comprises an outsourcing management unit managing outsourcing information of the outsourcer terminal and/or the outsourcee terminal; and wherein
the server device allows, between the outsourcer terminal and the outsourcee terminal, mutual application and approval of start of the outsourcing and mutual registration.

Item 3

The data management system of item 1 or 2, wherein the server device comprises a chat function, wherein
the outsourcer terminal and/or the outsourcee terminal comprises an input unit for inputting chat into the chat function, and wherein
the chat function is available between the outsourcer terminal and the outsourcee terminal.

Item 4

The data management system of item 3, wherein using the chat function, the server device notifies the outsourcee that the outsourcer shares the order container with the outsourcee.

Item 5

The data management system of any one of items 1 to 4, wherein
the order container comprises:
an order data storage unit allowing use of only the outsourcer;
an order data storage unit allowing use of only the outsourcee; and
an order data storage unit allowing sharing between the outsourcer and the outsourcee; and wherein
the outsourcer terminal and the outsourcee terminal comprise:
a data sharing authority management unit managing setting of whether to share or not to share data correlated with the order container with the outsourcer and/or the outsourcee,
the order container having therein an area dedicated to the outsourcer and/or the outsourcee and a sharing area, allowing selection of whether to share or not to share data correlated with an order.

Item 6

The data management system of any one of items 1 to 5, wherein
the server device comprises an order chat function correlated with the order container, wherein
the outsourcer terminal and/or the outsourcee terminal comprises an input unit inputting chat into the order chat function, and wherein
the server device comprises the order chat function separately for each order container, to thereby allow chat interaction separately for each order.

Item 7

The data management system of items 3 and 6, wherein the chat function and/or the order chat function sends a moving image, a still image, 3D shape data, text, a written text, and audio, the data sent being saved in the data storage unit, and wherein
when sending data by the order chat function, the data is correlated with the order container.

Item 8

The data management system of items 6 and 7, wherein the order chat function comprises, in a single order container:
an order chat function for the outsourcer;
an order chat function for the outsourcee; and an order chat function shared between the outsourcer and the outsourcee, and wherein there exist a plurality of order chat functions for a single order.

Item 9

The data management system of any one of items 3 to 8, wherein the chat function and/or the order chat function allows quotation of their respective chat utterances to another chat.

Item 10

The data management system of any one of items 1 to 9, wherein the outsourcee terminal comprises:

a working process input unit inputting working process information, based on an instruction document created in the outsourcer terminal; and a transmission unit transmitting the working process information to the server device, wherein the server device comprises a working process information storage unit storing working process progress status information for each of the order containers, wherein the outsourcer terminal and the outsourcee terminal comprise a display unit displaying information stored in the working process information storage unit of the server device, and wherein the working process information input is cable of being shared with an other terminal.

Item 11

The data management system of item 10, wherein the server device reports work progress status for each order to the outsourcer, using the order chat function, based on the information input to the working process information storage unit.

Item 12

The data management system of item 10 or 11, wherein the server device comprises a working process record creation unit creating a working record from working process information stored in the working process information storage unit storing product working process information, and wherein a working process record document is automatically created from working process information and is stored in a corresponding order container area.

Item 13

The data management system of item 11, wherein when the working process record document is stored in an order container, the data management system notifies that the working process record document has been stored with the chat function and/or the order chat function.

Item 14

The data management system of any one of items 1 to 13, wherein the outsourcer terminal and/or the outsourcee terminal comprises an instruction document creation and edit unit creating and/or editing the instruction document, to revise and/or newly create the instruction document, the instruction document creation and edit unit editing and/or newly creating the instruction document.

Item 15

The data management system of any one of items 1 to 14, wherein the outsourcer terminal and/or the outsourcee terminal comprises:

an approval application unit asking the outsourcer and/or the outsourcee for approval when revising and/or newly creating a written text such as an instruction document or a written contract shared; and an approval unit making approval when receiving an application for approval from the outsourcer and/or the outsourcee, and wherein the outsourcer and/or the outsourcee gives approval to a counterpart when the written text such as the instruction document or the written contract is revised and/or newly created.

Item 16

The data management system of item 15, wherein the outsourcee terminal comprises a sub-outsourcing request unit which, when an order difficult to be handled by the outsourcee is outsourced, outsources the order to a sub-outsource, and wherein when the sub-outsourcing request unit requests for sub-outsourcing, the instruction document edit unit describes name and address of the sub-outsourcee on the instruction document; the approval application unit of the outsourcee terminal applies for approval to the outsourcer terminal; and the approval unit of the outsourcer terminal approves, whereby the outsourcer terminal shares the order container with the sub-outsourcee terminal, to implement outsourcing to the sub-outsourcee.

Item 17

The data management system of item 15 or 16, wherein the approval application unit applies for approval using the chat function shared, to obtain approval by the chat function.

Item 18

The data management system of item 16 or 17, wherein the order container when requesting for sub-outsourcing comprises:

an area for the sub-outsourcee;

an area sharable between the outsourcee and the sub-outsourcee; and an area sharable among the outsourcer, the outsourcee, and the sub-outsourcee.

Item 19

The data management system of any one of items 14 to 18, wherein the order chat function includes:

an order chat function within a sub-outsourcee organization;

an order chat function shared between the outsourcee and the sub-outsourcee;

an order chat function shared among the outsourcer, the outsourcee, and sub-outsourcee.

Item 20

The data management system of any one of items 1 to 19, wherein when new addition or alteration is applied to the chat function and/or the order chat function, sharing of the order container, and shared data within the order container, it is notified by communication means communicating a message.

Item 21

The data management system of any one of items 3 to 20, wherein the chat function and/or the order chat function distinctively issues utterance needing no approval and utterance needing approval, ensuring easy distinguishableness among utterance needing no approval, utterance needing approval, and approved utterance by marking or differently coloring.

Item 22

The data management system of any one of items 1 to 21, wherein the outsourcer terminal correlates a past order container used in past outsourcing with a new order container, and wherein the outsourcer terminal and/or the outsourcee terminal browses a conversation history of the order chat function within the order container and/or data correlated therewith.

Item 23

The data management system of any one of items 8 to 22, wherein the outsourcer terminal comprises a receipt confirmation unit sending receipt of a technical product to the server device, wherein information sent from the receipt confirmation unit is recorded in a working process information storage unit of the order container, and wherein the outsourcer notifies the outsourcee and/or the sub-outsourcee of receipt of the technical product.

Item 24

The data management system of any one of items 3 to 23, wherein the outsourcer terminal comprises a refabrication request unit selecting an order wanted to be refabricated from past orders, to request for refabrication, wherein when refabrication is requested for via the refabrication request unit, the server device uses the chat function to notify the outsourcee that refabrication is requested for, allowing display of a link to the order container area in a chat.

According to the exemplary embodiment of the present invention, any format of data can be managed on an order-by-order basis, reducing the time and effort taken for the management of instruction documents or other data.

According to the exemplary embodiment of the present invention, conversations between the outsourcer and the outsourcee hitherto made by paper medium, telephone, mail, SMS, or facsimile can be performed through this system, providing a system effective for efficient work and for improving work-style.

According to the exemplary embodiment of the present invention, creation and storage of the instruction document and work records become simple.

According to the exemplary embodiment of the present invention, not only the instruction documents but also other written contracts can be managed, rendering simple the management of contract that has hitherto been complicated, such as outsourcing between a dental clinic and a dental laboratory.

According to the exemplary embodiment of the present invention, when issuing a technical instruction to a sub-outsourcee dental laboratory, the instruction and/or approval and confirmation of a dentist can be obtained in a simple manner.

According to the exemplary embodiment of the present invention, written contracts are correlated for each facility, preventing e.g. mistake of the written contracts.

The exemplary embodiment of the present invention ensures simple edit and approval of the instruction documents.

According to the exemplary embodiment of the present invention, edit histories of the instruction documents or the written contracts are saved, enabling reference thereto at any time.

According to the exemplary embodiment of the present invention, order placing to the sub-outsourcee can simply be made, contributing to increased business efficiency of the dental laboratory.

In the exemplary embodiment of the present invention, if there occurs a refabrication, an order wanted to be refabricated is selected for outsourcing, with the order being linked with the notification, enabling simple browsing of the instruction documents or data.

According to the exemplary embodiment of the present invention, by managing the sharing authority, browsing or sharing may be permitted only within each facility. As a result, since data and progress management can be performed, improvement in efficiency is expected as compared with the conventional management method when dividing the technical work.

According to the exemplary embodiment of the present invention, by inputting the working process information, current progress can appropriately be reported to the outsourcer.

BRIEF DESCRIPTION OF THE DRAWINGS

FIG. 5A shows an example of an order reception management screen appearing on an outsourcee terminal;

FIG. 5B shows an example of a management screen appearing when an order list is displayed for each clinic;

FIG. 10 shows an example of a patient data sending confirmation screen;

FIG. 12 shows an example of a screen of an order placing unit; and

DETAILED DESCRIPTION

A data management system of the present invention will now be described with reference to the accompanying drawings. It is to be noted that an embodiment shown below is a mere example of the present invention and that the present invention can also adopt various configurations without being limited to the following embodiment.

Figure 1:
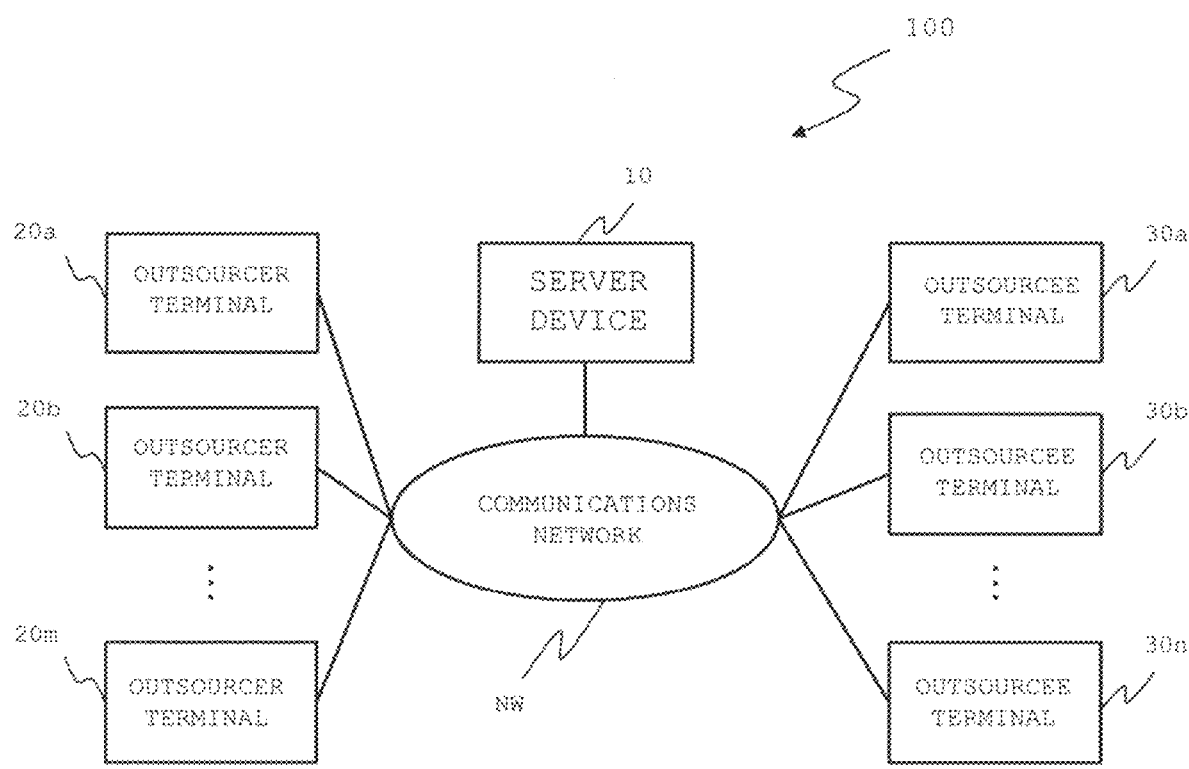
FIG. 1 is a block diagram showing a configuration example of a data management system according to an embodiment of the present invention.

FIG. 1 is a block diagram of a data management system 100 in the embodiment. The data management system 100 of the embodiment is configured to include a plurality of or a single server device 10, a single or a plurality of outsourcer terminals 20a to 20m (m: integer greater than or equal to 1), and a single or a plurality of outsourcee terminals 30a to 30n (n: integer greater than or equal to 1), which are communicable with one another via a communications network NW. Hereinafter, the outsourcer terminals 20a to 20m and the outsourcee terminals 30a to 30n may comprehensively be written as "outsourcer terminal 20" and "outsourcee terminal 30", respectively. The server device 10 need not necessarily be disposed, and either the outsourcer terminal 20 or the outsourcee terminal 30 may act also as the server device. The "communications network NW" will be written as "network NW".

The types of terminal units for use as the outsourcer terminal 20 and the outsourcee terminal 30 are not particularly limitative. Such terminal units may be various types of electronic equipment having communication functions, such as e.g. personal computers (PCs), tablets, smartphones, or cellular phones. Any terminal unit is available as long as it includes e.g. an arithmetic unit that is a central processing unit (CPU), a main memory unit in the form of a random access memory (RAM), and an auxiliary memory unit such as a hard disk drive (HDD), a solid state drive (SSD), or a flash memory. The terminal unit can further be any terminal including various input/output units, such as: a communication circuit connecting to the network NW, such as a network interface card; a display unit such as a display; and devices such as a keyboard and a mouse. The embodiment assumes a case where both the outsourcer terminal 20 and the outsourcee terminal 30 use the PCs.

The server device 10 can be any server including an arithmetic unit such as a CPU or a graphics processing unit (GPU), a main memory unit such as RAM, and an auxiliary memory unit such as HDD, SSD, or flash memory. The server device 10 may further include various input/output units, such as a communication circuit connecting to the network NW. A general computer unit is available as the server device 10.

The network NW used in the present invention is not particularly limitative as long as it is a communications network accessible to the server device 10. The Internet can ordinarily be used as such a network NW. Use of the Internet can reduce the cost of an ordering system of the present invention.

The network NW may be a virtual private network (which may hereinafter be referred to as "VPN") dedicated to the data management system of the present invention, built in the Internet. This can reduce the cost while enhancing the safety of the data management system. The network NW may be configured with a dedicated line, in place of the Internet, or may be configured from the combined dedicated line and the Internet.

The network NW may be a wired network, a wireless network, or a combination thereof. It is preferred that this network NW have enhanced security by various ways, such as using a dedicated line, encrypting transmission data, and authenticating a user who uses each client unit or the like.

Figure 2A:
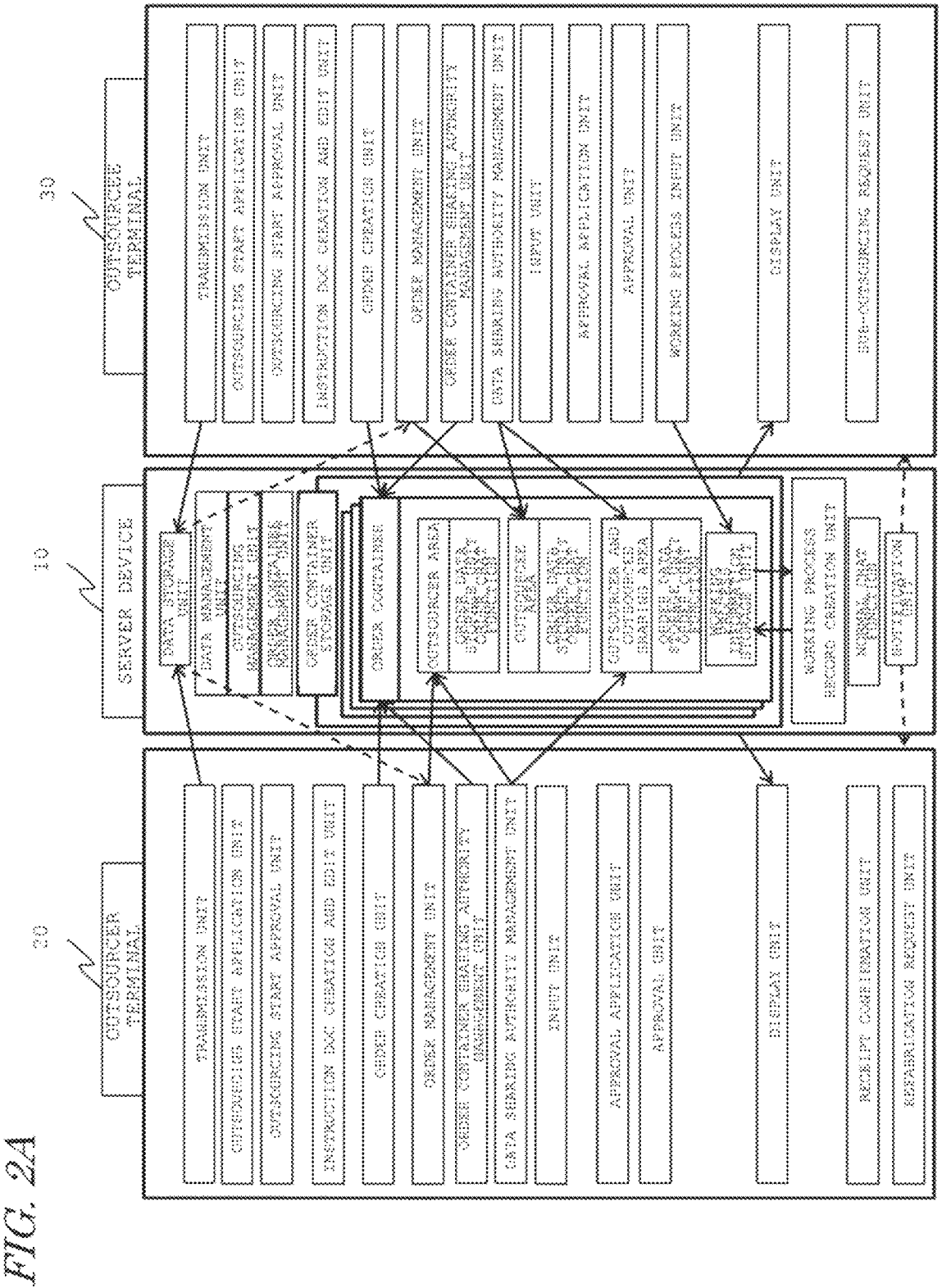
FIG. 2A is a block diagram showing an exemplary configuration of the data management system according to the embodiment of the present invention.

FIG. 2A shows an example of the embodiment. Referring to FIG. 2A, details of the embodiment will be described.

The outsourcer terminal 20 includes a transmission unit, an outsourcing start application unit, an outsourcing start approval unit, an instruction document creation and edit unit, an order creation unit, an order management unit, an order container sharing authority management unit, a data sharing authority management unit, an input unit, an approval application unit, an approval unit, a display unit, a receipt confirmation unit, and a refabrication request unit.

The transmission unit transmits various types of information to the server device 10, for storage in a data storage unit. In order to start outsourcing, the outsourcing start application unit applies for start of outsourcing to an outsourcee. When receiving an outsourcing start application from the outsourcee, the outsourcing start approval unit approves the application. The instruction document creation and edit unit creates and edits an instruction document, based on the user's operation. For each order, the order creation unit creates, in an order container storage unit of the server device 10, an order container to which data stored in the data storage unit can be assigned. The order management unit assigns data stored in the data storage unit to the order container. The order container sharing authority management unit shares the order container with the outsourcee. The data sharing authority management unit manages setting of whether to share or not to share data assigned to the order container with the outsourcee.

The input unit allows entering into a chat function and an order chat function, based on the user's operation.

The approval application unit asks the outsourcee for approval in the case that an instruction document or a written contract is altered and/or newly drawn up. The approval unit makes approval when an approval application is asked for from the outsourcee.

The display unit displays information stored in the server device 10.

The receipt confirmation unit notifies the outsourcee of receipt of a technical product made based on the instruction document. The refabrication request unit requests the outsourcee terminal 30 for refabrication of a dental technical product by the user's operation when the dental technical product has a defect or the like.

Among these, the transmission unit and the receipt confirmation unit are e.g. communication circuits. The display unit is e.g. a display. Other configuration elements except the transmission unit, receipt confirmation unit, and display unit are implemented by an arithmetic circuit such as a CPU executing a computer program stored in RAM.

The transmission unit transmits data to the server device 10. Examples of the sendable data include, but not limited thereto, document data such as instruction documents and written contracts, 3D shape data, moving images, still images, illustrations, audio data, text data, etc.

The outsourcing start application unit can apply for start of outsourcing with the outsourcee terminal 30. In the embodiment, outsourcing can be started by making an application for outsourcing and applying for start of outsourcing to obtain approval in the outsourcee's outsourcing start approval unit. However, these actions are mere examples. For example, when making an application for outsourcing in an outsourcing application unit, a written outsourcing contract may be attached so that application and approval of the outsourcing contract can be made in the same manner.

The outsourcing start approval unit can give approval in the case that the start of outsourcing is applied for from the outsourcee terminal 30 using its outsourcing start application unit.

The instruction document creation and edit unit accepts input of information for fabricating an outsourced product, to create an instruction document. In the case that the user edits an instruction document stored in the server device 10, information stored in the server device 10 is downloaded, to start the edit in the state where information described in the instruction document stored in the server device 10 is input at the time of editing. In the embodiment, information input to the instruction document creation and edit unit is information required to create an instruction document, such as patient name, methods of designing and fabrication, materials used, date of issue, name of a dentist who issued the instruction document and location of a hospital or a clinic where the dentist works, and name and location of a dental laboratory when the dental laboratory is a place where dental technical work is performed based on the instruction document. Other examples of input may include ordering date, patient information, product ordering number, and unique ID identifying a dental clinic.

The order creation unit can create an order container in the order container storage unit of the server device 10. The order container is a unit of data management provided for each order, and a set of data stored in the data storage unit are correlated with each other for each order. In the embodiment, the server device 10 creates an order container in response to data selection, but this is a mere example and not limitative. For example, creation of an order container by the server device 10 may be triggered by storage of a file, such as storage of an instruction document in the server device 10 or storage of 3D shape data in the data storage unit of the server device 10. Alternatively, the server device 10 may create an order container to which data is unassigned, in response to input of information on order.

The order management unit can correlate data stored in the data storage unit of the server device 10 with the order container created in the order creation unit.

The order container sharing authority management unit can select whether to share or not to share an order container created in the order creation unit with any outsourcee.

The data sharing authority management unit can select whether to share or not to share data correlated with an order in the order management unit with the outsourcee sharing a corresponding order container. If it is selected to share, the data sharing authority management unit stores data in an outsourcer and outsourcee sharing area. If it is selected not to share, the data sharing authority management unit stores data in an outsourcer area. Although the embodiment is configured to allow selection of whether to share/not to share, this is not limitative. Sharing may be essential, or sharing/unsharing may automatically be sorted by providing a sharing rule that uses data type, file name, etc.

The input unit can enter information into a chat function and/or an order chat function, in response to the user's input. The format of entered data is typically text information. Without limitation to text information, however, it may include e.g. still images, moving images, 3D shape data, illustrations, audio data, etc. Other types of data may further be included therein. In the embodiment, if the entered information is information other than the text information, it is saved in the data storage unit. If data is sent by the order chat function, the data is correlated with a corresponding order container.

When an instruction document or a written contract is revised and/or newly created, the approval application unit can apply for approval to the counterpart having the approval authority, to thereby request for approval. At this time, the counterpart for approval application is not always one, and the approval may be applied for to a plurality of counterparts. The approval application unit can determine whether the counterpart has the approval authority, based on the sharing authority.

The approval unit can make approval if a request for approval is issued by the approval application unit of the outsourcer terminal 20 as a result of revision work of an instruction document or a written contract in the outsourcee terminal 30.

The display unit can display data stored in the server device 10.

The receipt confirmation unit can notify the outsourcee of receipt of a dental technical product. In the embodiment, if receipt of a technical product is confirmed, the receipt confirmation unit sends receipt confirmation information to the server device 10, which in turn stores receipt information in a working process information storage unit of a corresponding order container.

The refabrication request unit can simply request for refabrication in the case e.g. that there is something wrong, that a dental technical product cannot be fitted to the patient, or that a dental technical product is damaged within its warranty period. "Simply" means that refabrication can be requested for by a simple procedure. More specifically, if wanted to request for refabrication of a dental technical product, when the user designates the dental technical product, information specifying an order container area at the time of creating the dental technical product is described as a link in the chat function. The request for refabrication is then notified to the outsourcee in charge. The refabrication requester can easily request the outsourcee in charge to refabricate by only designating a dental technical product to be remade. Since utilization of the link enables easy access to the order container, the outsourcee in charge requested for refabrication can easily acquire information required for refabrication.

The outsourcee terminal 30 includes a transmission unit, an outsourcing start application unit, an outsourcing start approval unit, an instruction document creation and edit unit, an order creation unit, an order management unit, an order container sharing authority management unit, a data sharing authority management unit, an input unit, an approval application unit, an approval unit, a working process input unit, a display unit, and a sub-outsourcing request unit.

The transmission unit transmits various types of information to the server device 10, for storage in the data storage unit.

In order to start outsourcing, the outsourcing start application unit applies for start of outsourcing to the outsourcer. When receiving an outsourcing start application from the outsourcer, the outsourcing start approval unit approves the application. The instruction document creation and edit unit creates and edits an instruction document. For each order, the order creation unit creates, in the order container storage unit of the server device 10, an order container with which data stored in the data storage unit can be correlated. The order management unit correlates data stored in the data storage unit with the order container. The order container sharing authority management unit shares the order container with the outsourcer. The data sharing authority management unit manages setting of whether to share or not to share data correlated with the order container, with the outsourcer.

The input unit allows entering into a chat function and an order chat function, based on the user's operation.

The approval application unit asks the outsourcer for approval in the case that an instruction document or a written contract is altered and/or newly drawn up. The approval unit performs approval when an approval application is asked for from the outsourcer. The working process input unit inputs working process information of an order and sends the working process information to the server device 10 in order to store it in the working process information storage unit of a corresponding order container of the server device 10.

The display unit displays information stored in the server device 10.

The sub-outsourcing request unit makes a request to a sub-outsourcee if the outsourcee cannot fulfill the order.

Among these, the transmission unit and the working process input unit are e.g. communication circuits. The display unit is e.g. a display. Other configuration elements except the transmission unit and display unit are implemented by an arithmetic circuit such as a CPU that executes a computer program stored in RAM.

The transmission unit transmits data to the server device 10. Examples of the sendable data include, but not limited thereto, document data such as instruction documents and written contracts, 3D shape data, moving images, still images, illustrations, audio data, text data, etc.

The outsourcing start application unit can apply for start of outsourcing with the outsourcer terminal 20. In the embodiment, outsourcing can be started by making an application for outsourcing and applying for start of outsourcing to obtain approval in the outsourcer's outsourcing start approval unit. However, these actions are mere examples. For example, when making an application for outsourcing in an outsourcing application unit, a written outsourcing contract may be attached so that application and approval of the outsourcing contract can be made in the same manner.

The outsourcing start approval unit can give approval in the case that the start of outsourcing is applied for from the outsourcee terminal 30 using its outsourcing start application unit.

The instruction document creation and edit unit accepts input of information for editing and creating a dental technical product, to edit and/or draw up an instruction document. In the case of editing an instruction document stored in the server device 10, information stored in the server device 10 is downloaded, to start the edit in the state where information described in the instruction document stored in the server device 10 is input at the time of editing. In the embodiment, examples of information edited in the instruction document creation and edit unit include methods of designing and fabrication, materials used, name and location of a dental laboratory when the dental laboratory is a place where dental technical work is performed based on the instruction document, and detailed design parameters. However, these are mere examples. Although in the embodiment the outsourcee can draw up instruction documents as well, only editing may be possible in a limitative manner.

The order creation unit can create an order container in the order container storage unit of the server device 10. In the embodiment, as an example, it selects data to create an order container. Additionally, for example, creation of an order container may be triggered by storage of a file, such as storage of an instruction document in the server device 10 or storage of 3D shape data in the data storage unit of the server device 10. Alternatively, the server device 10 may create an order container with which data is uncorrelated, in response to input of information on order.

In the case that the outsourcee has not introduced the system of the embodiment, outsourcing may possibly be made in a conventional manner. In such a case, since the outsourcee terminal 30 can also create an order container, data management by the system of the embodiment can be effected in the outsourcee terminal 30.

The order management unit can correlate data stored in the data storage unit of the server device 10 with the order container created in the order creation unit.

The order container sharing authority management unit can select whether to share or not to share an order container created in the order creation unit with any outsourcer.

The data sharing authority management unit can select whether to share or not to share data correlated with an order in the order management unit with the outsourcer sharing a corresponding order container. If shared, the data is stored in an outsourcer and outsourcee sharing area, whereas if not shared, it is stored in an outsourcee area. Although the embodiment is configured to allow selection of whether to share/not to share, this is not limitative and sharing may be essential, or sharing/unsharing may automatically be sorted by providing a sharing rule that uses data type, file name, etc.

The input unit can ordinarily enter information into a chat function and/or an order chat function. The enterable data format can be not only text information, but also e.g. still images, moving images, 3D shape data, illustrations, or audio data, but is not limited thereto. In the embodiment, if the entered information is information other than the text data, it is saved in the data storage unit. If data is sent by the order chat function, the data is correlated with a corresponding order container.

When an instruction document or a written contract is revised and/or newly created, the approval application unit can request the counterpart having the approval authority, for approval. At this time, the counterpart for approval application is not always one, and the approval may be applied for to a plurality of counterparts.

The approval unit can make approval if a request for approval is issued by the approval application unit of the outsourcer terminal 20 as a result of revision work of an instruction document or a written contract in the outsourcee terminal 30.

The working process input unit can enter working process information on an order to store the working process information in the working process information storage unit of a corresponding order container of the server device 10.

The display unit can display data stored in the server device 10.

The sub-outsourcing request unit can make a request to a sub-outsourcee if the outsourcee cannot fulfill the order. When information on the sub-outsourcee is entered, the sub-outsourcing request unit uses the instruction document creation and edit unit to enter the information on the sub-outsourcee into an instruction document, to notify the outsourcer of request for approval using the approval application unit. When the outsourcer approves, the outsourcee and/or the sub-outsourcee is notified of approval so that data is shared with the sub-outsourcee. Although the embodiment is configured to allow outsourcing up to the secondary outsourcee, without being limited thereto the number of the outsourcees can be increased in a similar procedure.

The server device 10 includes: the data storage unit that stores data of instruction documents, written contracts, work records, 3D shape data, still images, moving images, illustrations, documents, audio data, etc. sent from the outsourcer terminal 20 and/or the outsourcee terminal 30; a data management unit for managing who owns the data; an outsourcing management unit that manages outsourcing relationships approved by the outsourcing start application unit and the outsourcing start approval unit of the outsourcer terminal 20 and/or the outsourcee terminal 30; an order container management unit that manages sharing of an order container, based on an instruction from the order container sharing authority management unit of the outsourcer terminal 20 and/or the outsourcee terminal 30; the order container storage unit that stores an order container created in the order creation unit of the outsourcer terminal 20 and/or the outsourcee terminal 30; a working process record creation unit that creates a working process record by using an order container created in the order creation unit and information of the working process information storage unit in the order container; and a notification unit that issues a notification in the case e.g. that chat is updated in a chat function for chatting between the terminals, that data is shared, or that an approval application or an approval is accepted.

The data storage unit has a function of storing data sent from the outsourcer terminal 20 and/or the outsourcee terminal 30. Examples of data include, but not limited thereto, instruction documents, written contracts, work records, 3D shape data, still images, moving images, illustrations, documents, audio data, etc.

The data management unit manages who owns data stored in the data storage unit.

The outsourcing management unit manages outsourcing started in the outsourcer and outsourcee.

The order container management unit can manage sharing of an order container, based on an instruction from the order container sharing authority management unit of the outsourcer terminal 20 and/or the outsourcee terminal 30.

The order container storage unit can store an order container created in the order creation unit of the outsourcer terminal 20 and/or the outsourcee terminal 30.

The order container is created in the order creation unit of the outsourcer terminal 20. The order container area of the embodiment includes an outsourcer area, an outsourcee area, an outsourcer and outsourcee sharing area, and the working process information storage unit.

The outsourcer area is an area that only the outsourcer who has outsourced an order can browse/edit, and includes an order data storage unit and an order chat function.

The outsourcee area is an area that only the outsourcee who has accepted order outsourcing can browse/edit, and includes an order data storage unit and an order chat function.

The outsourcer and outsourcee sharing area is an area that the outsourcer and the outsourcee can browse/edit, and includes an order data storage unit and an order chat function.

The order chat function allows data accepted for input in the input unit of each terminal and entered into the order chat function to be stored in a corresponding order data storage unit of an area where an order chat exists. The order chat function displays link information. Examples of the entered data include, but not limited thereto, instruction documents, work records, 3D shape data, texts, still images, moving images, illustrations, documents, audio data, etc. Although the order chat function of the embodiment is configured to be assigned to each of the outsourcer area, the outsourcee area, and the outsourcer and outsourcee sharing area, this is not limitative. For example, configuration may be such that each order container has a single order chat function.

The working process information storage unit stores working process information in the case that a working process is entered that corresponds to an order sent from the working process input unit of the outsourcee terminal 30. Such a configuration enables management of correlating data shared only in the interior of the outsourcer and/or the outsourcee with an order. Examples of data referred to herein include, but not limited thereto, data on a dental technical product in the middle of design, a processing path used in a CAD/CAM unit, slice data used in a 3D printer, documents, etc.

The order chat function and/or the chat function allows chatting between and/or within facilities. Talk in a chat function can be copied for citation from the chat function to another chat. Use of this function enables for example: consultations and inquiries regarding a contract; consultations and inquiries required in performing a technical work; data transfer required in outsourcing; notification of sharing of an order container; report on work progress using working process information; notification of creation of a working process record by the working process record creation unit; notification of a request for approval, or notification when an approval request is approved and/or rejected.

The notification unit issues a notification in the case e.g. that there occur update of chat and/or sharing of an order container, and new processing or alteration of shared data in an order container, or that an approval application or an approval is accepted. Examples of the method of notification include, but not limited thereto, display in the chat function and/or the order chat function of the present system, sending of a notification to SMS, and sending of a notification to e-mail.

Figure 2B:
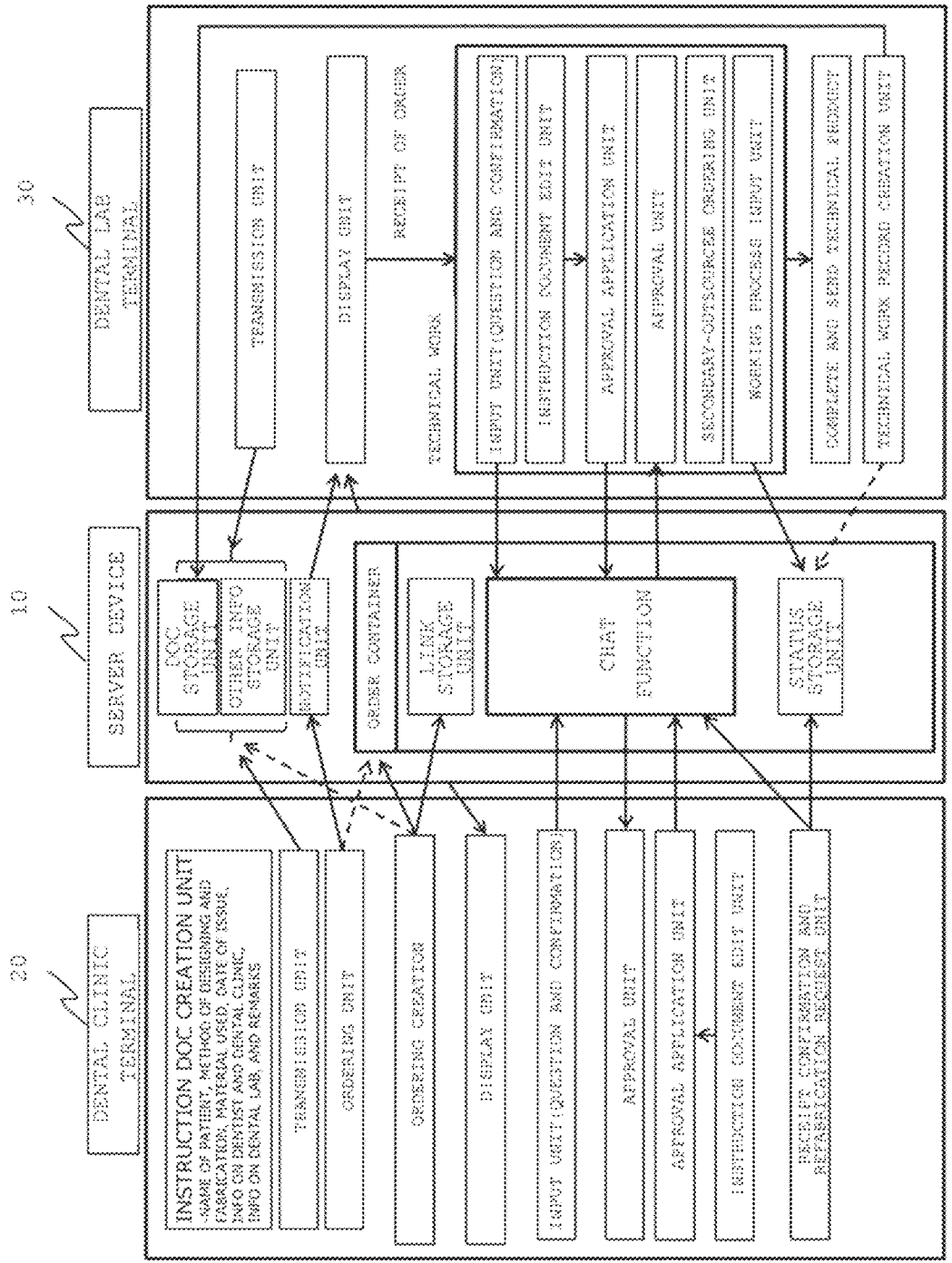
FIG. 2B is a block diagram showing a more specific configuration example of the data management system according to the embodiment of the present invention.

FIG. 2B is a block diagram showing a more specific configuration example of the data management system according to the exemplary embodiment. The outsourcer terminal 20 and the outsourcee terminal 30 are described specifically as a dental clinic terminal and a dental laboratory terminal, respectively.

Figure 2C:
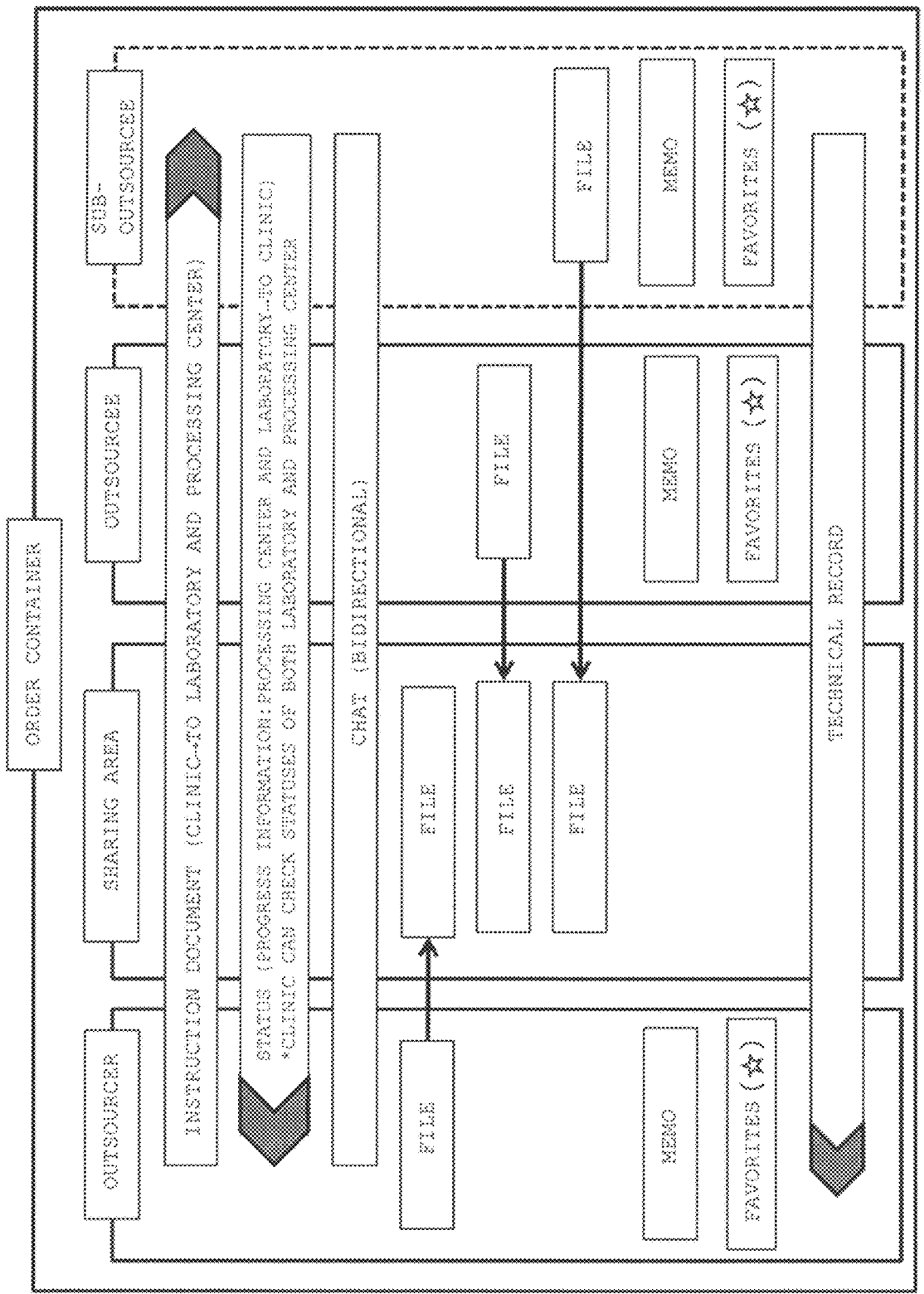
FIG. 2C is a block diagram showing a specific configuration example of an order container mounted in the data management system according to the embodiment of the present invention, as well as showing data transition within the order container.

FIG. 2C is a block diagram showing a specific configuration example of an order container mounted in the data management system according to the exemplary embodiment, as well as showing data transition within the order container. For each order, the order container shown in FIG. 2C is configured in which there are provided for a data area dedicated to an outsourcer, a data area dedicated to an outsourcee, and a data area dedicated to a sub-outsourcee. A sharing area is also prepared that each of the outsourcer, outsourcee, and sub-outsourcee can use for the purpose of e.g. sharing data. Each facility can select whether to share data saved in the data area of the each facility. Shared data is moved to the sharing area, in which link of the data is affixed and/or the data is copied.

Figure 3:
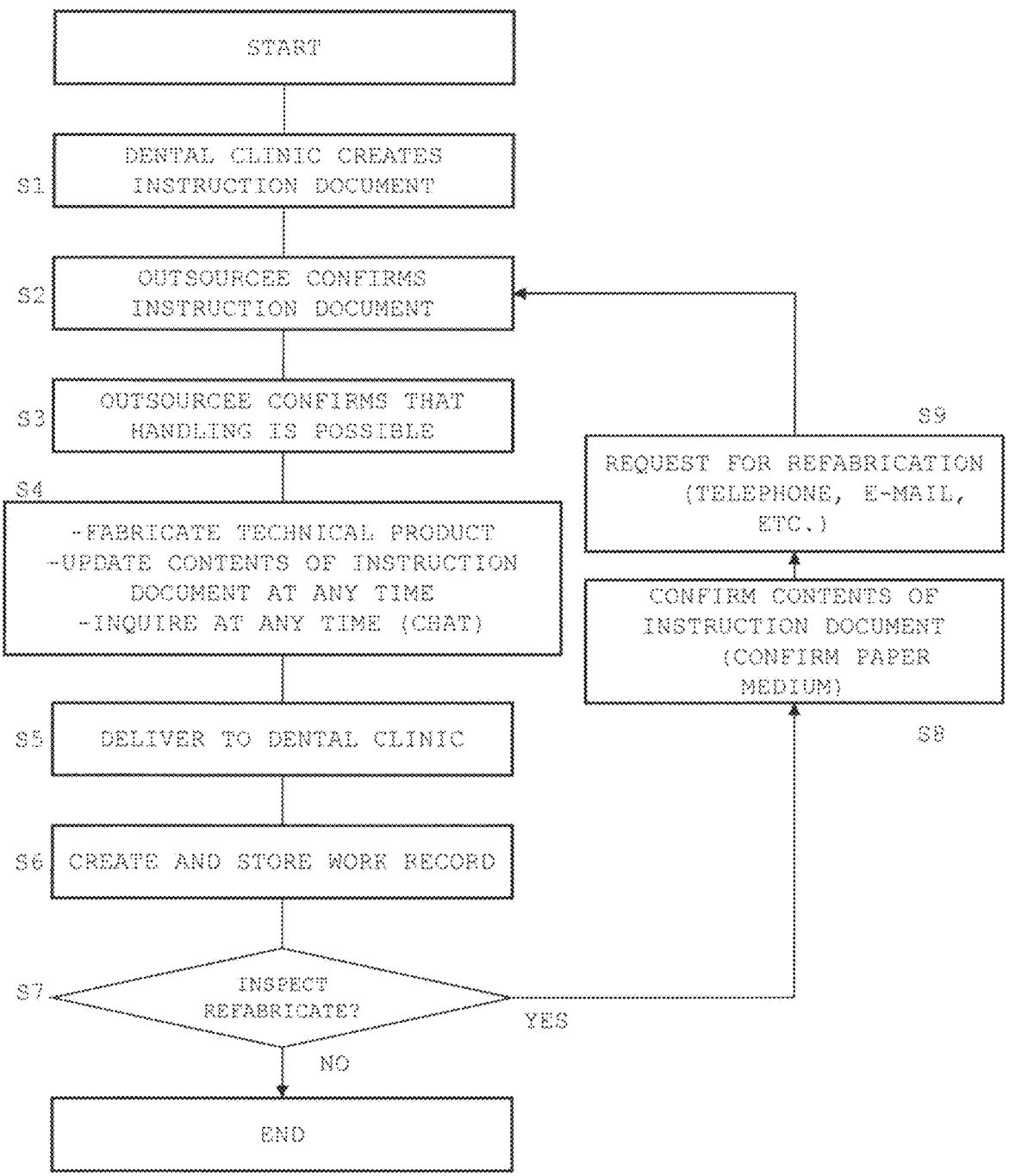
FIG. 3 is a flowchart showing a general procedure of fabricating a dental. technical product.
Figure 4:
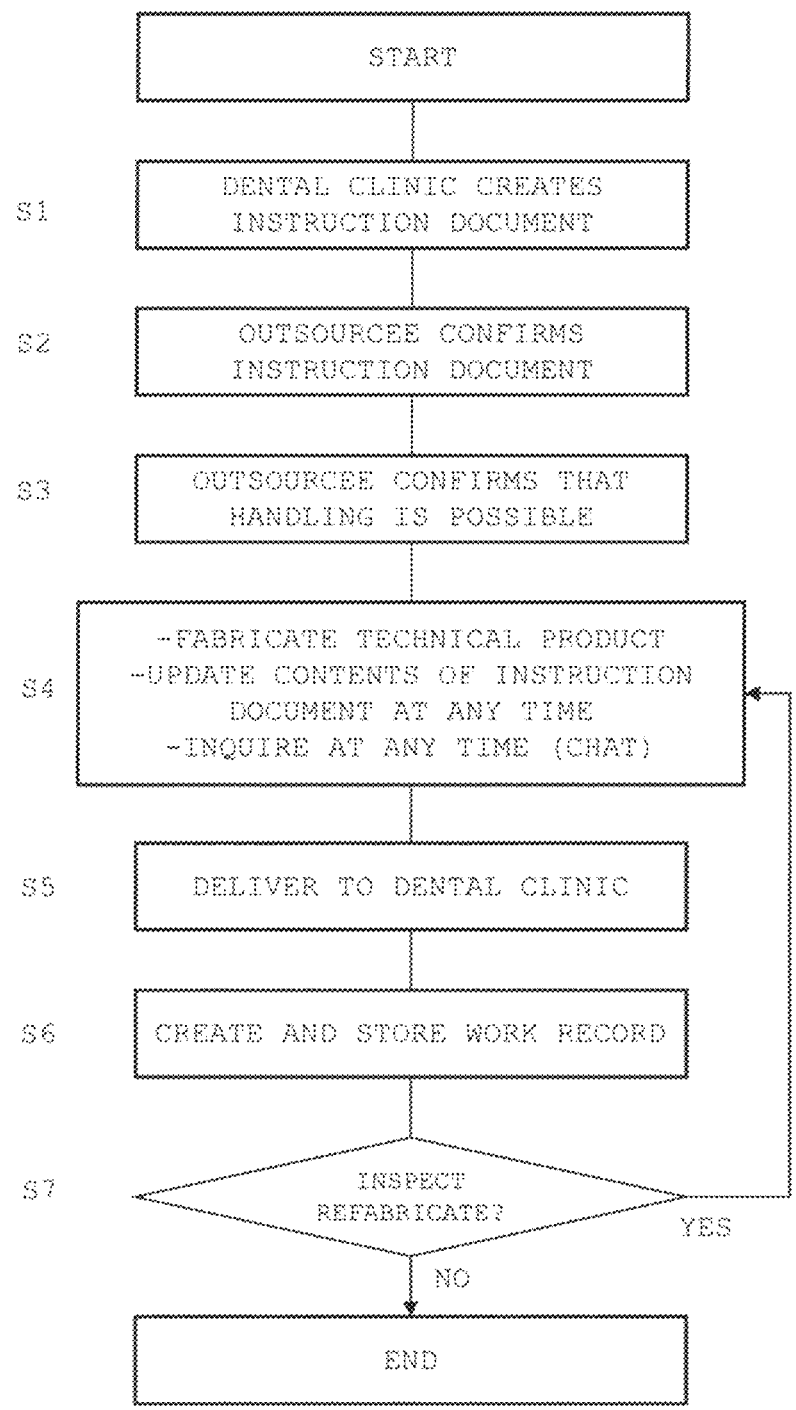
FIG. 4 is a flowchart showing a dental technical product fabrication procedure according to the embodiment of the present invention.

FIG. 3 is a flowchart showing a general procedure of fabricating a dental technical product. By contrast, in the embodiment, a dental technical product is made in a different procedure. FIG. 4 is a flowchart showing a dental technical product fabrication procedure according to the embodiment. Hereinafter, for convenience of understanding, description will be given while comparing the outline of flow of the dental technical product fabrication procedure of the embodiment with that of the general procedure.

At step S1 of FIGS. 3 and 4, a dental clinic or a dentist creates an instruction document. In general, a paper instruction document is created and delivered together with a patient tooth model to a dental laboratory (FIG. 3).

In the embodiment (FIG. 4), on the other hand, instead of the paper instruction document, e.g. a dentist uses the outsourcer terminal 20 to issue an instruction document in the instruction document creation and edit unit, and stores the instruction document in the data storage unit to correlate it with an order container. As regards the patient tooth model, 3D data in the patient's oral cavity is acquired, and stored in the data storage unit to correlate it with an order container. Alternatively, the tooth model may be transported as before.

At step S2 of FIGS. 3 and 4, an outsourcee dental laboratory confirms the instruction document. Generally, e.g. a dental technician confirms the paper instruction document (FIG. 3).

In the embodiment (FIG. 4), on the other hand, the outsourcee terminal 30 displays the instruction document.

At step S3 of FIGS. 3 and 4, the outsourcee dental laboratory confirms that it can deal with producing a dental technical product, based on the instruction document.

At step S4 of FIGS. 3 and 4, the dental laboratory fabricates the dental technical product. Although fabricated based on the instruction document, confirmation points may occur. Traditionally, the dental technician has made inquiries using telephone, e-mail, facsimile, SMS, or the like (FIG. 3). At this time, the dental laboratory and the dental clinic discusses with other while referring to the instruction document. Since a large amount of instruction documents are stored in the dental clinic and the dental laboratory, however, it takes a lot of time to prepare the instruction document at hand. Management of contents of inquiries is also time-consuming.

In the embodiment (FIG. 4), on the other hand, an order container on the server device 10 is correlated with instruction documents, data necessary for technical work, an order chat function, etc., so that information can be shared between the outsourcer terminal 20 and the outsourcee terminal 30. Inquiries can therefore be made simpler than making inquiries in the existing method. When the user of the outsourcer terminal 20 and/or the outsourcee terminal 30 uses the order chat correlated with the order container, the contents of an inquiry and reply thereto can be correlated with the order, facilitating the management. In the case that there is an omission in the instruction document or that there is a change after discussion between the dental clinic and the dental laboratory, the instruction document is revised using the instruction document creation and edit unit so that if approved as a result of application for approval, revision of the instruction document can simply be achieved.

At step S5 of FIGS. 3 and 4, when a technical product is completed, it is delivered to the dental clinic. The delivery is assumed to be made using means such as transport or handover or means for delivery of 3D data or data such as processing path.

At step S6 of FIGS. 3 and 4, the outsourcee creates a work record. The work record has hitherto been created and kept on paper (FIG. 3).

In the embodiment (FIG. 4), on the other hand, the outsourcee terminal 30 automatically creates a dental work record using working process information entered when producing a technical product. After confirmation and operation by the user of the dental laboratory, the dental work record is saved and shared with the outsourcer. At this time, the user of the outsourcee terminal 30 can enter e.g. information that is lacking in the working process information, to add the information to the working process information.

At step S7 of FIGS. 3 and 4, the outsourcer inspects a technical product delivered, and, if there is no problem, the technical product is fitted to the interior of the patient's oral cavity. If the product has a problem, a request for refabrication is issued. Up until now, the outsourcer has confirmed a paper instruction document, as shown at step S8 of FIG. 3, and has requested the outsourcee for refabrication, as shown at step S9 of FIG. 3, using telephone, male, SMS, etc. At this time, the outsourcer and the outsourcee need time and effort to find an instruction document and to find processing data used at that time and the patient tooth model. The embodiment enables the dental clinic to request for refabrication from this system.

In the case that this system issues a request for refabrication (YES at step S7 of FIG. 4), the request is issued in the state where information required for technical work for refabrication is correlated therewith. The laboratory therefore need not find past data.

Figure 5A:
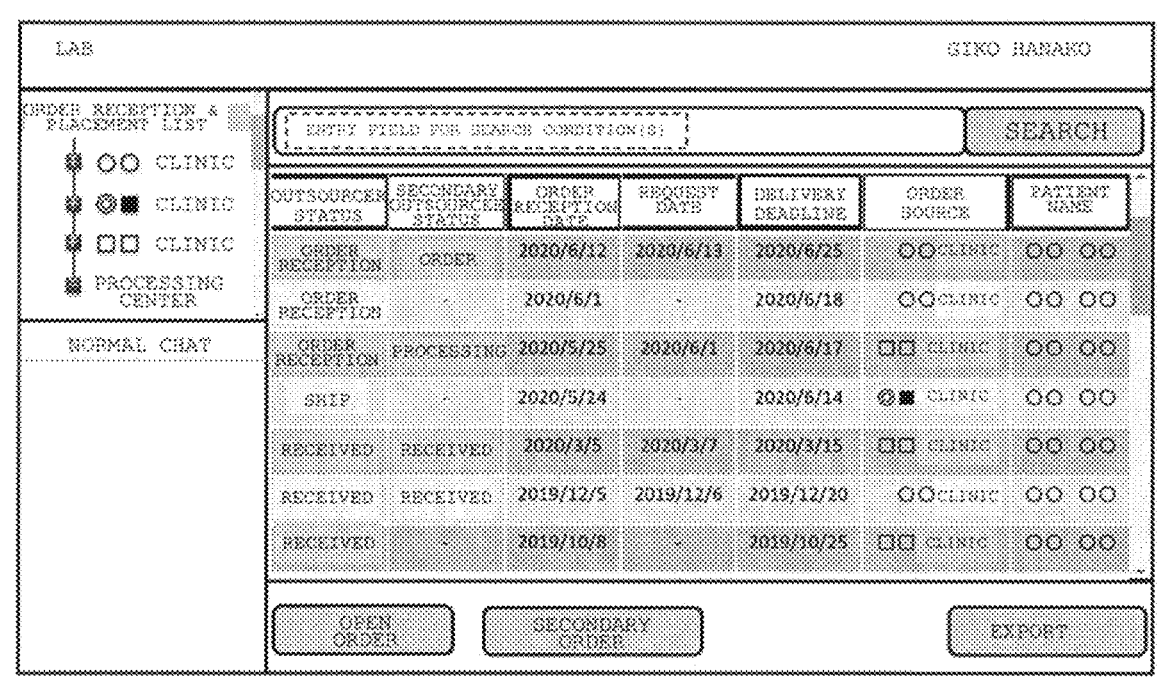
Figure 5B:
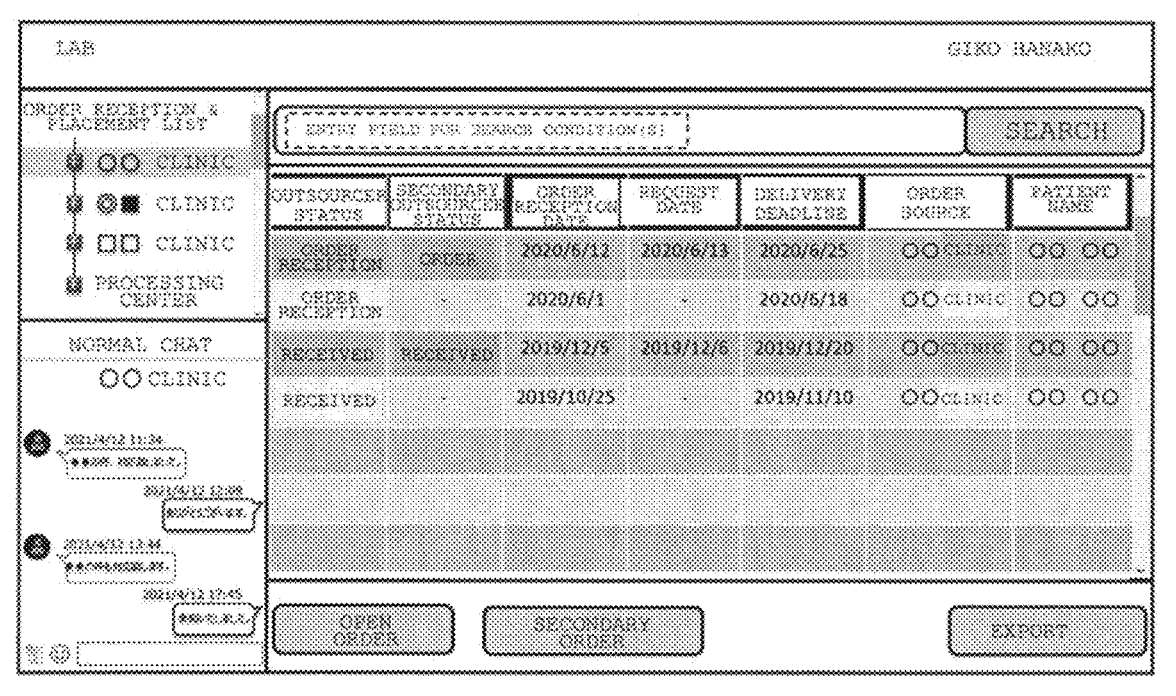

FIG. 5A shows an example of an order management screen appearing on the outsourcee terminal 30 of the embodiment. The embodiment displays, but not limited thereto, clinic's working process information, secondary-outsourcee's working process information, order reception date, date of request to secondary outsourcee, order source, patient name, and delivery deadline. Permutation and extraction can be made with these parameters. Search can be made with a "Search" button. For example, working process information for "order reception" from a clinic can be extracted, or searched in the order source. An order list can be displayed for each clinic, and, when displaying an order list extracted by a clinic name, a normal chat of the clinic is displayed. FIG. 5B shows an example of a management screen appearing when an order list is displayed for each clinic.

The working process information contains "order placement", "order reception", "designing", "processing", "finishing", "ready to ship", "in transit", "received", "modified", and "cancelled", each of which varies with progress of work. Although the contents of the working process information are listed above in a non-limitative manner, configuration may be e.g. such that each clinic or each laboratory can freely enter its working process information.

An "export" button allows exporting an order reception and placement information list displayed on the order reception management screen. There are no particular restrictions on the export format, and export is enabled in a general format such as text, table, image, etc.

The normal chat function enables sending of data uncorrelated with an order, response thereto, or discussion thereon.

A "secondary order" button allows issuance of secondary order of an order in selection to another dental laboratory, based on an instruction of a dentist. At this time, the instruction document edit unit describes name and address of a secondary outsourcee on an instruction document; the approval application unit of the outsourcee terminal 30 applies for approval to the outsourcer; and the approval unit of the outsourcer terminal 20 makes approval, whereby an order container area is shared with the secondary outsourcee so that secondary outsourcing is carried out.

An "open order" button allows display of an order in selection.

Figure 6:
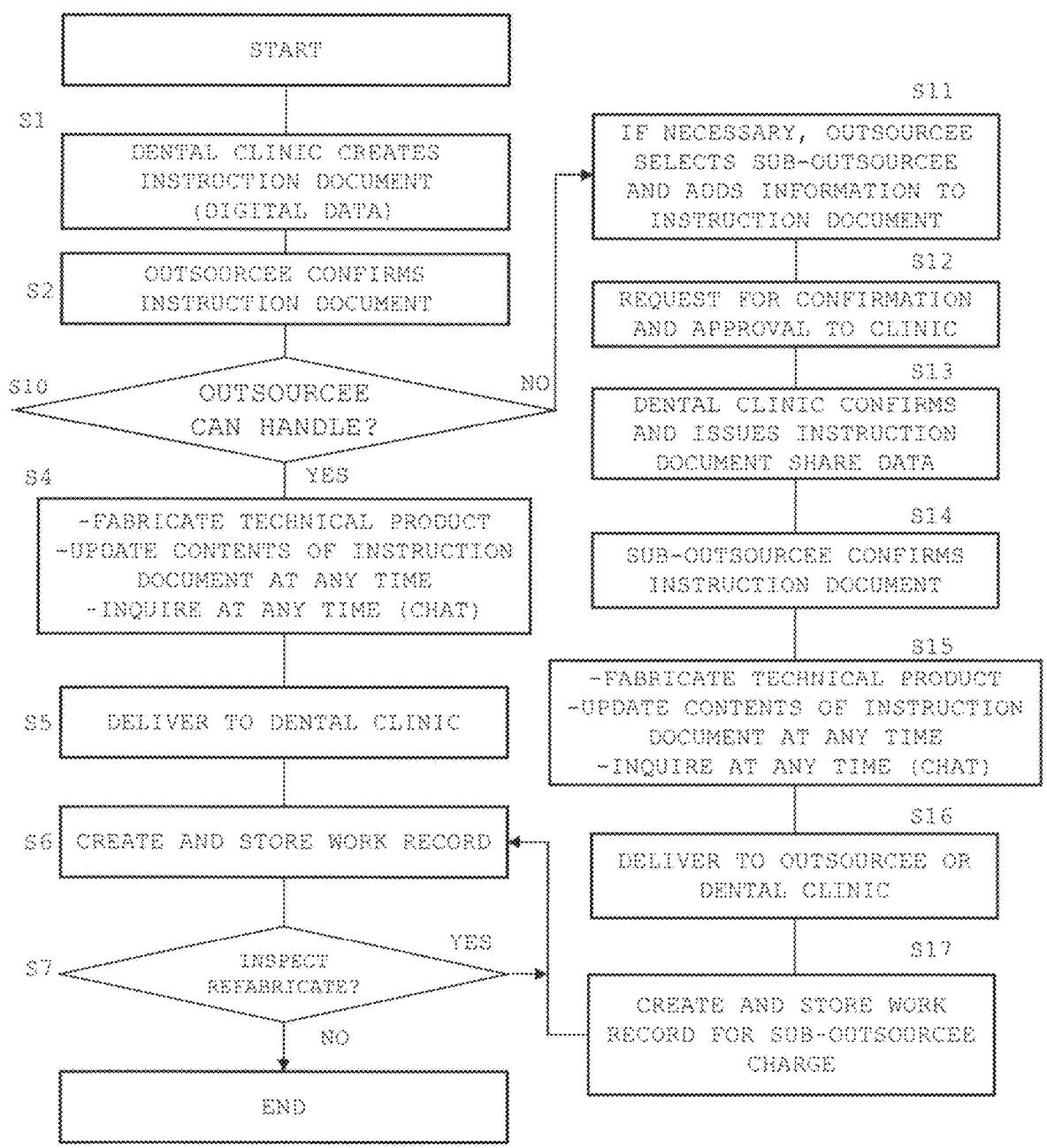
FIG. 6 is a flowchart of an instruction document in the case that an outsourcee cannot deal with an order.

FIG. 6 is a flowchart of an example of the embodiment, in which, when a laboratory accepts outsourcing of an order incapable of handling by itself, the laboratory describes detailed design parameters on an instruction document to outsource the order to e.g. a secondary outsourcee such as a processing center. Some (steps S1, S2, S4 to S7) of the steps of FIG. 6 are the same as the steps of FIG. 4 having the same numbers. Only brief mention thereof will be given below.

At step S1, a dental clinic creates an instruction document about a technical product by use of the outsourcer terminal 20, to share data with the outsourcee terminal 30 that is the outsourcee. At step S2, the outsourcee confirms the instruction document, and at step S10, the outsourcee determines whether it can deal with producing the technical product. If affirmative, the process goes to step S4, whereas if negative, the process goes to step S11.

At step S11, regarding the order that the outsourcee cannot deal with by itself, the outsourcee requests another laboratory and/or a processing center as the sub-outsourcee to undertake part or all of the technical work, using the outsourcee terminal 30. Also regarding the sub-outsourcing, Japanese law requires to perform the technical work, based on the dentist's instruction document. The outsourcee terminal 30 thus uses the instruction document edit unit to add necessary information to the instruction document, to modify the document.

At step S12, the approval application unit of the outsourcee terminal 30 asks a dentist to check the instruction document modified by adding necessary information and applies for approval thereof. When at step S13 the dentist approves via the outsourcer terminal 20, the revised instruction document is issued from the dental clinic. When the instruction document is revised, the sub-outsourcee shares the instruction document as well as data necessary for the technical work.

At step S15, the sub-outsourcee fabricates a technical product and e.g. updates the contents of the instruction document. This process is the same as that at step S4.

After completion of the technical work in the sub-outsourcee, at step S16, the sub-outsourcee delivers the technical product to the outsourcer or the primary outsourcee, and at step S17, creates a work record of work that it is in charge of. The sub-outsourcee stores the work record in the form of allowing the primary outsourcee and/or the outsourcer dental clinic to browse it. In the case that the technical product is delivered to the primary outsourcee, only part of the technical work is often outsourced. The primary outsourcee carries out the remaining work on the technical product delivered from the sub-outsourcee, delivers it to the outsourcer dental clinic, and creates a work record. After the delivery, the primary outsourcee stores the work record in such a manner that the outsourcer dental clinic can browse it.

Figure 7:
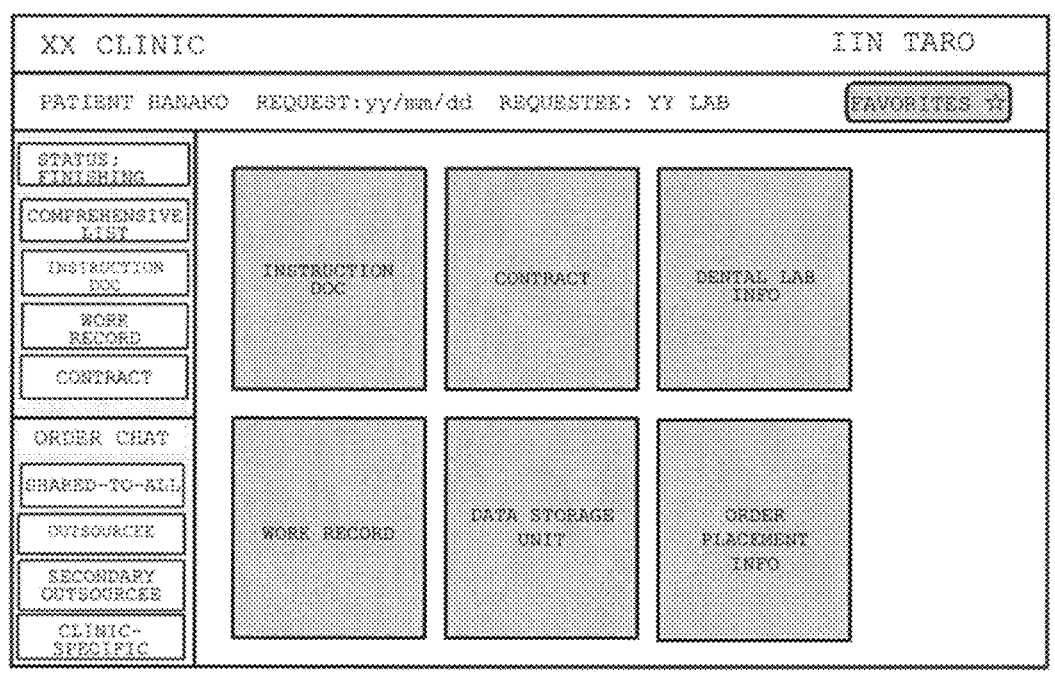
FIG. 7 shows an example of an order display screen appearing on an outsourcer terminal.

FIG. 7 shows an example of an order display screen appearing on the outsourcer terminal 20. The order display screen displays name of logged-in user, patient information, request date, and requestee, with buttons of instruction document, work record, written contract, chat, and memo data storage unit arranged thereon. The "instruction document" button allows display of an instruction document of an order in selection. The "written contract" button allows display of a list of contracts with an outsourcee of the order in selection. When selecting a contract wanted to be displayed from the contract list, a written contract appears. The "work record" button is displayed only in the case that a corresponding work record is registered, and when clicked, a work record corresponding to the order appears. The "chat" buttons provide for and display chats of shared-to-all, between dental clinic and dental laboratory, between dental clinic and sub-outsourcee dental laboratory, and between dental laboratory and sub-outsourcee dental laboratory. Unless sub-outsourcing is effected, there appear no chat buttons between dental clinic and dental laboratory, between dental clinic and sub-outsourcee dental laboratory, and between dental laboratory and sub-outsourcee dental laboratory.

There is also a memo chat function, providing a chat area not shared with another dental clinic and any dental laboratory. The chat area allows free description about things to be recorded for an order, and about information wanted to be shared within each facility regarding the order. In the case that a dental clinic or a dental laboratory has a plurality of user accounts, sharing may be permitted only within the interior of each organization. The "data storage unit" button is a button allowing display of a list of data that the logged-in user is authorized to browse, saved in a data storage area. Data sent from the outsourcer terminal 20 and the outsourcee terminal 30 is stored in the data storage unit so that the logged-in user who has stored data in the data storage unit can designate the sharing authority management of whether to share or not to share each data. Although in the embodiment the log-in user can designate the sharing authority management, the sharing authority imparting method is not limited thereto, and users within the same facility may be able to manage the sharing authority. The sharing authority management may employ the form of automatically imparting the authority, based on the naming rule or the form of imparting the sharing authority, depending on the type of an uploader used when storing data. For example, in the case of uploading data by chat, the sharing authority may automatically be imparted to the counterpart of the chat.

Figure 11:
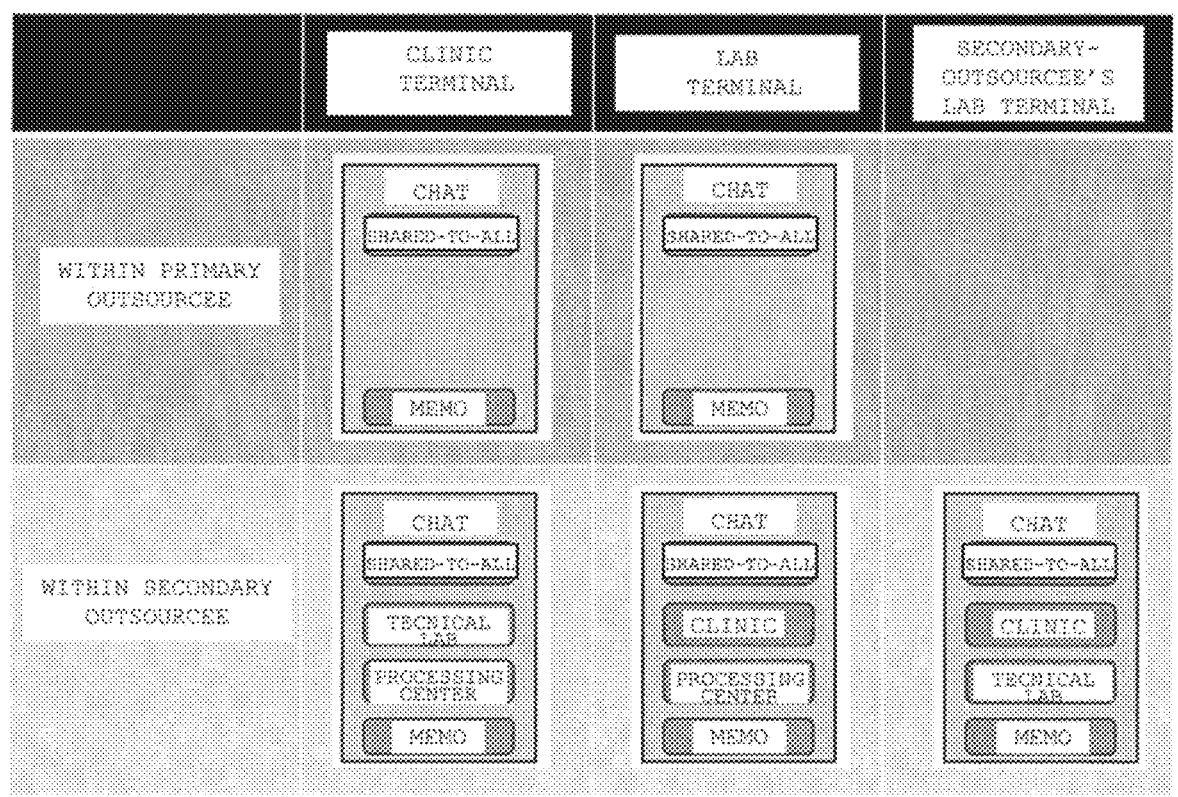
FIG. 11 shows a pattern example of a chat group.

FIG. 11 shows a pattern example of a chat group. Although the embodiment employs the example including up to the sub-outsourcee, further chat functions are added thereto if the number of the sub-outsourcees increases up to a tertiary or quartic outsourcee.

Figure 8:
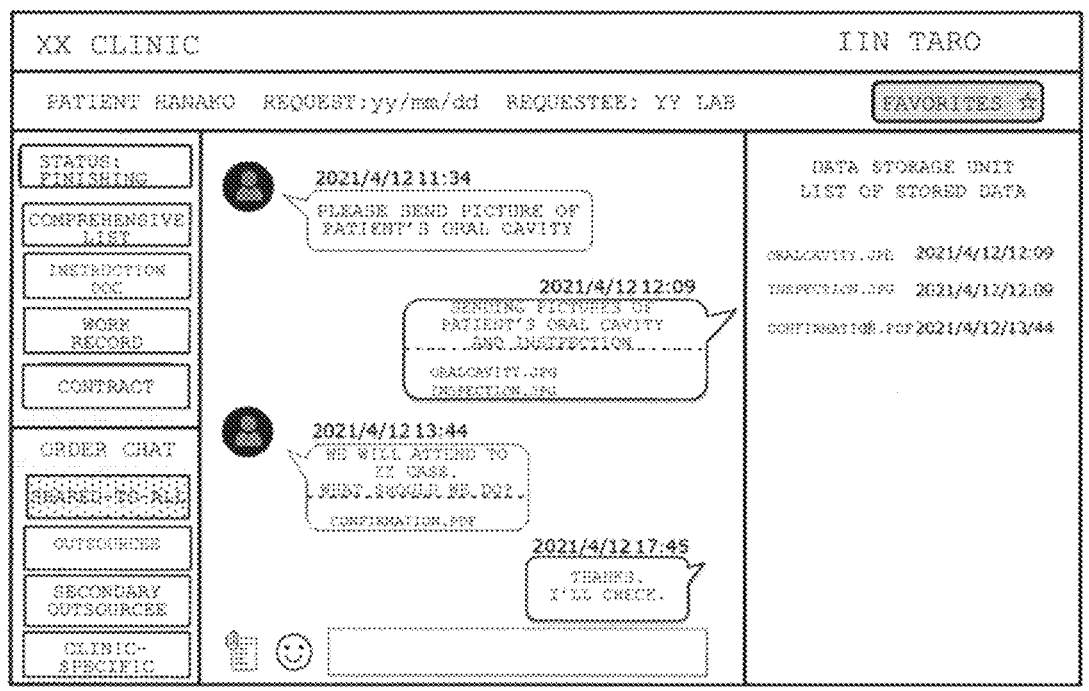
FIG. 8 shows an example of a chat screen.

FIG. 8 shows an example of a chat screen. Here, a shared-to-all chat screen is exemplified. The chat screen enables sending of messages and data as shown. The messages are sent with sender and sending time accompanied. The data are saved in the data storage area, and data sent by the order chat function is correlated with a corresponding order container and is shared in a link format in the chat function.

The format of data sent by the chat function is not particularly limitative, and any form of data can be attached such as still images, moving images, documents, text data, 3D shape data, and audio data. The attached data is displayed in list form as a shared file list.

The chat function enables utterance needing no approval and utterance needing approval to be issued in a distinguished manner. The utterance needing approval and approved utterance are marked and/or differently colored, thereby facilitating distinction.

Figure 9:
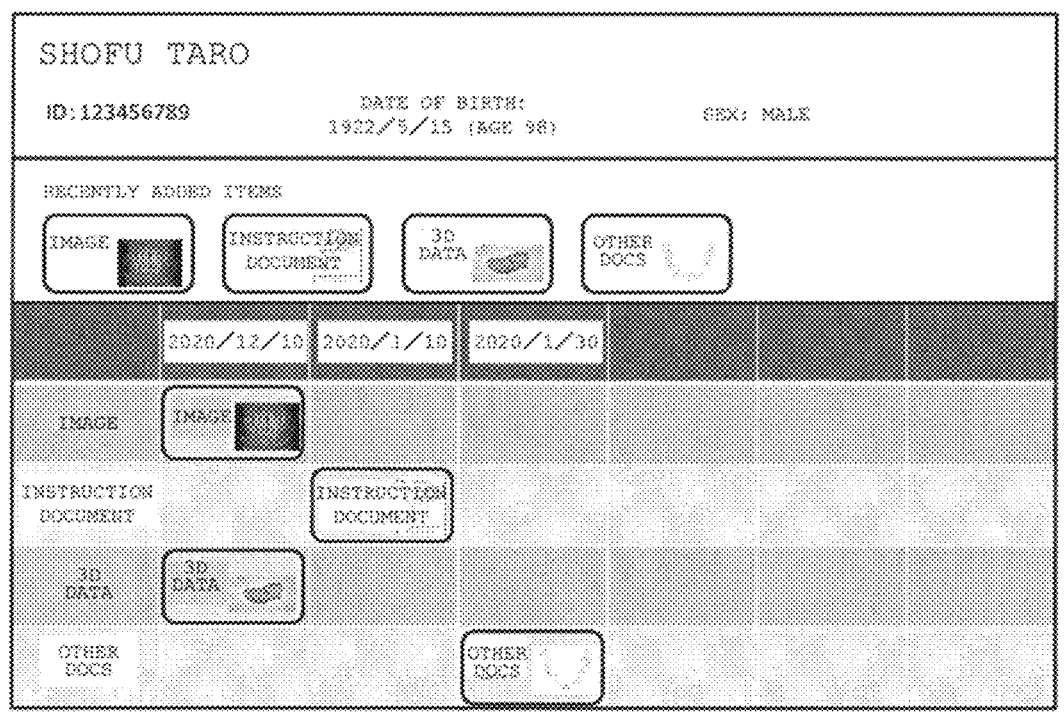
FIG. 9 shows an example of a patient data management screen.

FIG. 9 shows an example of a patient data management screen appearing on the outsourcer terminal 20. The screen displays information on patient in display, recently added patient data, and a patient data matrix. Although the matrix of FIG. 9 provides a matrix display of sent data by date and type, this is not limitative.

This screen enables data on a patient to be sent to the server device 10 in a manner correlated with the patient by drag and drop on a personal computer. At this time, there is no particular regulation on sendable data, allowing data of any file format to be sent. Plural pieces of data can be sent together, and in the case of sending plural pieces of data at a time, they are registered together as a series.

Figure 10:
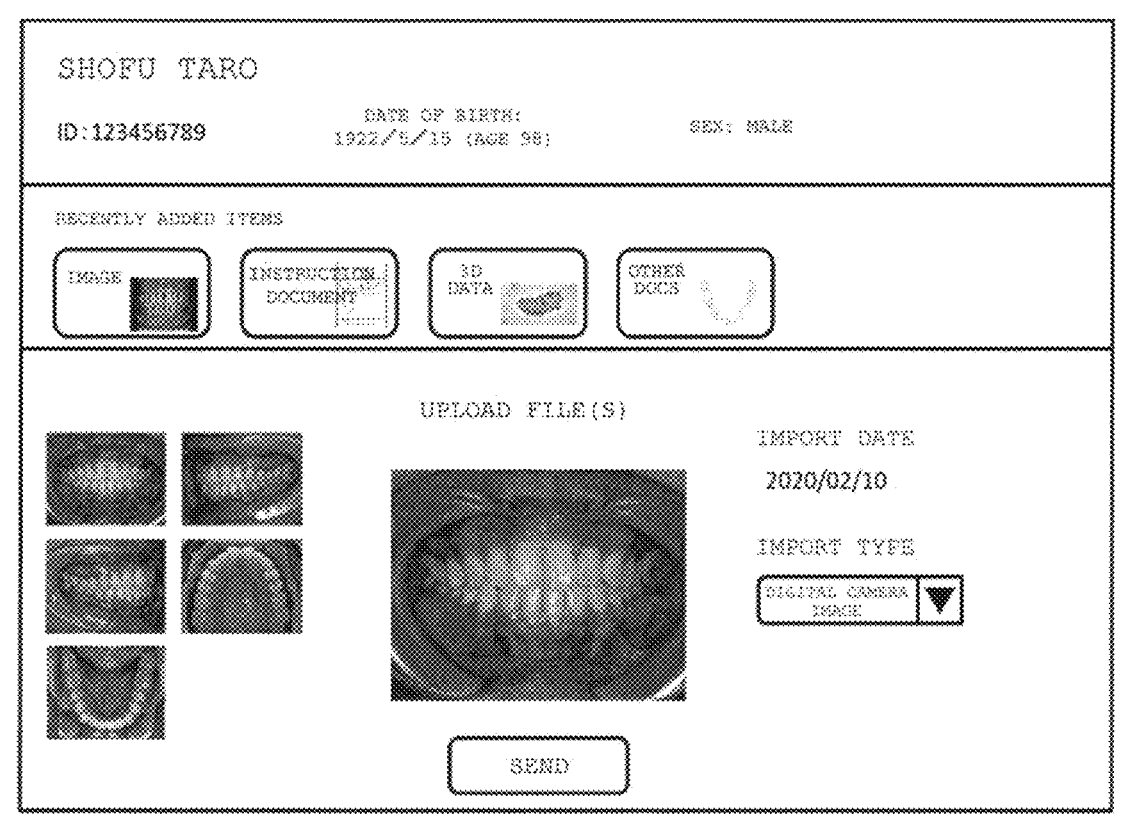

FIG. 10 shows a sending confirmation screen appearing when drag and drop occurs onto the screen of FIG. 9. The patient information is correlated with data to be sent, and type tags may be added thereto depending on the data type. The added tags are classified by the types of FIG. 9 and saved in their respective storage areas. Examples of selectable type tags include, but not limited thereto, "instruction document", "3D shape data", "digital camera image", "CT", "surgical record", "illustration", "video", "other document", and "other data". In the case of sending plural pieces of data, configuration may be such that only part of data can be selected and sent on the sending confirmation screen.

Figure 13:
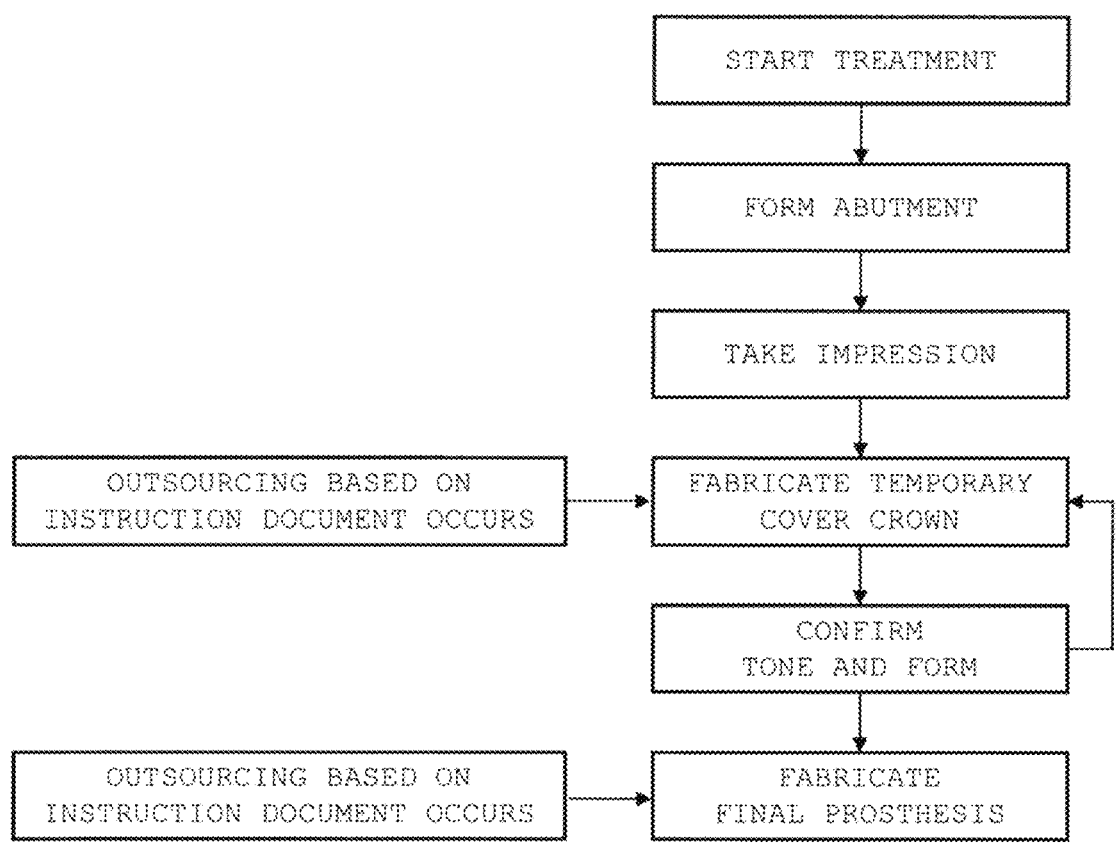
FIG. 13 is an explanatory view of an example where a plurality of instruction documents are issued for each order.

FIG. 12 shows an example of a screen of an order placing part. FIG. 13 is a flowchart of an example where a plurality of instruction documents are issued for a single case. In the dental care, as shown in the diagram, plural sheets of order may occur regarding the same case, and a plurality of instruction documents may be issued. Particularly, in the case of fabricating a temporary cover crown before fabrication of a final technical product, a technical product identical in form and color to but different only in material from the final technical product is fabricated to confirm the shape and color tone before fabrication of the final technical product. Although in this case the dental laboratory uses data for fabrication of the temporary cover crown to fabricate the final technical product, if the data and instruction documents are not correlated with the order, management of the data and the instruction documents may become complicated.

In the embodiment, when creating a new order container, it can be correlated with a past order container as a related case, enabling browse and/or download of conversation history on the order chat function in the past order container, and of data correlated therewith. This makes it possible to browse and/or use conversation information, etc. of the past order in the chat function at any time in the case of e.g. taking over data for the temporary cover crown or the like, leading to increased efficiency in the technical work.

Although the preferred embodiment of the present invention has hereinbefore be described in an exemplary manner, the present invention is not intended to be limited to the above embodiment, and naturally could adopt any form without departing from the gist of the present invention.

The data management system according to the present invention is useful to simplify data sharing between a dental clinic and a dental laboratory, to thereby reduce the time and effort taken for data management.

What is claimed is:

1. A data management system comprising: an outsourcer terminal of an outsourcer, the outsourcer terminal outsourcing a fabrication by an instruction document; an outsourcee terminal of a outsourcee, the outsourcee terminal receiving at least one of outsourcing or sub-outsourcing; and a server device, the outsourcer terminal, the outsourcee terminal, and the server device being connected via a network and sharing data with one another, the outsourcer terminal comprising:

a transmission unit transmitting data in the outsourcer terminal to the server device to store the data into a data storage unit of the server device;

an order creation unit creating an order container in an order container storage unit of the server device for each order, the data stored in the data storage unit being correlated with the order container;

an order management unit correlating the data stored in the data storage unit with the order container;

an order container sharing authority management unit sharing the order container with the outsourcee; and a display unit displaying information saved in the server device, the server device comprising:

the data storage unit storing data;

a data management unit managing a proprietary authority of data stored in the data storage unit;

the order container storage unit storing an order container with which the data stored in the data storage unit is correlated, for each order created in the order creation unit of the outsourcer terminal and/or an order creation unit of the outsourcee terminal;

an order container management unit managing sharing of the order container, based on an instruction from the order container sharing authority management unit of the outsourcer terminal and/or an order container sharing authority management unit of the outsourcee terminal; and a notification unit, when modification and/or data addition is applied to the order container shared by the order container sharing authority management unit, issuing a notification to the outsourcer and/or the outsourcee, the outsourcee terminal comprising:

a transmission unit transmitting data in the outsourcee terminal to the server device to store the data into the data storage unit of the server device;

the order creation unit creating an order container in the order container storage unit of the server device for each order, the data stored in the data storage unit being correlated with the order container;

an order management unit correlating the data stored in the data storage unit with the order container;

the order container sharing authority management unit sharing the order container with the outsourcer; and a display unit displaying information saved in the server device, the server device, for each order, correlating any format of data element stored therein with the order container, for management.

2. The data management system of claim 1, wherein the outsourcer terminal and/or the outsourcee terminal comprises:

an outsourcing start application unit for starting outsourcing with the outsourcer terminal and/or the outsourcee terminal; and an outsourcing start approval unit approving an application filed from the outsourcing start application unit, wherein the server device comprises an outsourcing management unit managing outsourcing information of the outsourcer terminal and/or the outsourcee terminal; and wherein the server device allows, between the outsourcer terminal and the outsourcee terminal, mutual application and approval of start of the outsourcing and mutual registration of the outsourcing information.

3. The data management system of claim 1, wherein the server device comprises a normal chat function, wherein the outsourcer terminal and/or the outsourcee terminal comprises an input unit for inputting chat into the normal chat function, and wherein the normal chat function is available between the outsourcer terminal and the outsourcee terminal.

4. The data management system of claim 3, wherein using the normal chat function, the server device notifies the outsourcee that the outsourcer shares the order container with the outsourcee.

5. The data management system of claim 3, wherein the normal chat function and/or the order chat function sends a moving image, a still image, 3D shape data, text, a document, audio data, and an illustration, the data sent being saved in the data storage unit, and wherein when sending data by the order chat function, the data is correlated with the order container.

6. The data management system of claim 3, wherein
the server device keeps utterances in a chat quotable to another chat in the normal chat function and/or the order chat function.

7. The data management system of claim 3, wherein
the normal chat function and/or the order chat function distinctively issues utterance needing no approval and utterance needing approval, with mutually distinguishable display of utterance needing no approval, utterance needing approval, and approved utterance.

8. The data management system of claim 3, wherein
the outsourcer terminal comprises a refabrication request unit selecting an order wanted to be refabricated from past orders, to request for refabrication, wherein
when refabrication is requested for via the refabrication request unit, the server device uses the normal chat function to notify the outsourcee that refabrication is requested for, allowing display of a link to the order container area in a chat.

9. The data management system of claim 1, wherein
the order container comprises:
an order data storage unit allowing use of only the outsourcer;
an order data storage unit allowing use of only the outsourcee; and
an order data storage unit allowing sharing between the outsourcer and the outsourcee; and wherein
the outsourcer terminal and the outsourcee terminal comprise:
a data sharing authority management unit managing setting of whether to share or not to share data correlated with the order container with the outsourcer and/or the outsourcee,
the order container having therein an area dedicated to the outsourcer and/or the outsourcee and a sharing area, the outsourcer terminal and the outsourcee terminal accepting selection of whether to share or not to share data correlated with an order.

10. The data management system of claim 1, wherein
the server device comprises an order chat function correlated with the order container, wherein
the outsourcer terminal and/or the outsourcee terminal comprises an input unit inputting chat into the order chat function, and wherein
the server device comprises the order chat function separately for each order container, to thereby manage chat interaction separately for each order.

11. The data management system of claim 10, wherein
the order chat function comprises, in a single order container:
an order chat function for the outsourcer;
an order chat function for the outsourcee; and
an order chat function shared between the outsourcer and the outsourcee, and wherein
the server device manages a plurality of order chat functions for a single order.

12. The data management system of claim 11, wherein
the outsourcer terminal comprises a receipt confirmation unit sending receipt of a technical product to the server device, wherein
information sent from the receipt confirmation unit is recorded in a working process information storage unit storing working process progress information of the order container, and wherein
the outsourcer notifies the outsourcee and/or the sub-outsourcee of receipt of the technical product.

13. The data management system of claim 1, wherein
the outsourcee terminal comprises:
a working process input unit inputting working process information, based on an instruction document created in the outsourcer terminal; and
a transmission unit transmitting the working process information to the server device, wherein
the server device comprises a working process information storage unit storing working process progress status information for each of the order containers, wherein
the outsourcer terminal and the outsourcee terminal comprise a display unit displaying the working process progress status information stored in the working process information storage unit of the server device, and wherein
the working process information input is cable of being shared with an other terminal.

14. The data management system of claim 13, wherein
the server device reports work progress status for each order to the outsourcer, using the order chat function, based on the information input to the working process information storage unit.

15. The data management system of claim 14, wherein
when the working process record document is stored in an order container, the data management system notifies that the working process record document has been stored with the normal chat function and/or the order chat function.

16. The data management system of claim 13, wherein
the server device comprises a working process record creation unit creating a working record from working process information stored in the working process information storage unit storing product working process information, and wherein
the server device creates a working process record document based on working process information, to store the working process record document in a corresponding order container area.

17. The data management system of claim 1, wherein
the outsourcer terminal and/or the outsourcee terminal comprises an instruction document creation and edit unit creating and/or editing the instruction document, to revise and/or newly create the instruction document, the instruction document creation and edit unit editing and/or newly creating the instruction document.

18. The data management system of claim 17, wherein
the order chat function includes:
an order chat function within a sub-outsourcee organization;
an order chat function shared between the outsourcee and the sub-outsourcee;
an order chat function shared among the outsourcer, the outsourcee, and sub-outsourcee.

19. The data management system of claim 1, wherein
the outsourcer terminal and/or the outsourcee terminal comprises:
an approval application unit asking the outsourcer and/or the outsourcee for approval when revising and/or newly creating a written text such as an instruction document or a written contract shared; and
an approval unit making approval when receiving an application for approval from the outsourcer and/or the outsourcee, and wherein the outsourcer and/or the outsourcee gives approval to a counterpart when the written text such as the instruction document or the written contract is revised and/or newly created.

20. The data management system of claim 19, wherein the outsourcee terminal comprises a sub-outsourcing request unit which, when an order difficult to be handled by the outsourcee is outsourced, outsources the order to a sub-outsourcee, and wherein when the sub-outsourcing request unit requests for sub-outsourcing, the instruction document edit unit describes name and address of the sub-outsourcee on the instruction document; the approval application unit of the outsourcee terminal applies for approval to the outsourcer terminal; and the approval unit of the outsourcer terminal approves, whereby the outsourcer terminal shares the order container with the sub-outsourcee terminal, to implement outsourcing to the sub-outsourcee.

21. The data management system of claim 20, wherein the order container when requesting for sub-outsourcing comprises:

an area for the sub-outsourcee;

an area sharable between the outsourcee and the sub-outsourcee; and an area sharable among the outsourcer, the outsourcee, and the sub-outsourcee.

22. The data management system of claim 19, wherein the order container comprises a chat function shared between the outsourcee terminal and the outsourcer terminal, wherein the approval application unit applies for approval using the chat function shared, to obtain approval.

23. The data management system of claim 1, wherein when new addition or alteration is applied to the normal chat function and/or the order chat function, sharing of the order container, and shared data within the order container, it is notified by means such as e-mail or SMS.

24. The data management system of claim 1, wherein the outsourcer terminal correlates a past order container used in past outsourcing with a new order container, and wherein the outsourcer terminal and/or the outsourcee terminal browses a conversation history of the order chat function within the order container and/or data correlated therewith.

* * * * *